(12) United States Patent
Karp et al.

(10) Patent No.: US 11,490,663 B2
(45) Date of Patent: Nov. 8, 2022

(54) INFANT SLEEP GARMENT

(71) Applicant: Happiest Baby, Inc., Los Angeles, CA (US)

(72) Inventors: Harvey Karp, Los Angeles, CA (US); Angie Lee, Los Angeles, CA (US)

(73) Assignee: HB Innovations, Inc., Los Angeles, CA (US)

( * ) Notice: Subject to any disclaimer, the term of this patent is extended or adjusted under 35 U.S.C. 154(b) by 272 days.

(21) Appl. No.: 16/282,091

(22) Filed: Feb. 21, 2019

(65) Prior Publication Data

US 2019/0313702 A1 Oct. 17, 2019

Related U.S. Application Data

(60) Provisional application No. 62/633,529, filed on Feb. 21, 2018.

(51) Int. Cl.
| | |
|---|---|
| *A41B 13/06* | (2006.01) |
| *A47G 9/08* | (2006.01) |
| *A47D 15/00* | (2006.01) |
| *A61M 21/02* | (2006.01) |

(52) U.S. Cl.
CPC ............ *A41B 13/065* (2013.01); *A47G 9/083* (2013.01); *A61M 21/02* (2013.01); *A41B 2300/30* (2013.01); *A41B 2400/32* (2013.01); *A41B 2400/44* (2013.01); *A47D 15/008* (2013.01)

(58) Field of Classification Search
CPC ... A41B 13/065; A41B 13/06; A41B 2400/44; A47G 9/083; A47D 15/005; A41D 11/00

USPC .......... 2/69.5; 5/29, 38, 734, 618, 624, 648, 5/504.1

See application file for complete search history.

(56) References Cited

U.S. PATENT DOCUMENTS

| | | | | |
|---|---|---|---|---|
| 779,809 | A * | 1/1905 | Sherick | A41D 11/00 2/75 |
| 1,292,351 | A * | 1/1919 | Milkes | A41D 11/00 2/84 |
| 1,332,400 | A | 3/1920 | Johnson | |
| 1,403,030 | A * | 1/1922 | Janzow | A41D 15/002 2/75 |
| 1,802,540 | A * | 4/1931 | Schmidt | A47D 15/008 2/69.5 |
| 1,897,258 | A | 2/1933 | Jenne | |
| D90,696 | S | 9/1933 | Caldwell | |

(Continued)

FOREIGN PATENT DOCUMENTS

| | | | |
|---|---|---|---|
| AT | 162244 B | * | 2/1949 |
| AU | 2010212430 | | 1/2011 |

(Continued)

OTHER PUBLICATIONS

Oval Crib, Fine Woodworking, http://www.finewoodworking.com/readerproject/2009/11/11/oval-crib, Nov. 11, 2009.

(Continued)

*Primary Examiner* — Khoa D Huynh
*Assistant Examiner* — Grace Huang
(74) *Attorney, Agent, or Firm* — Akerman LLP

(57) ABSTRACT

A sleep garment for an infant may include an enclosure for enclosing the infant. The enclosure may include one or more accommodation features such as a support element to position under the legs of the infant to elevate the feet, a weight element to position over the infant, or both.

20 Claims, 22 Drawing Sheets

(56) References Cited

U.S. PATENT DOCUMENTS

| | | | |
|---|---|---|---|
| D128,488 S | 7/1941 | Buckner | |
| 2,328,938 A * | 9/1943 | Wilson | A41B 13/06 |
| | | | 128/873 |
| 2,374,712 A * | 5/1945 | Steigerwald | A47G 9/083 |
| | | | 128/872 |
| 2,401,026 A * | 5/1946 | Steigerwald | A41B 13/06 |
| | | | 128/873 |
| 2,462,165 A * | 2/1949 | Condon | A41B 13/06 |
| | | | 2/69.5 |
| D158,030 S | 4/1950 | Wagner | |
| 2,508,110 A | 5/1950 | Hansen | |
| 2,523,422 A | 9/1950 | Dunn | |
| 2,530,464 A * | 11/1950 | Haman | A41B 13/06 |
| | | | 2/69.5 |
| 2,546,057 A * | 3/1951 | Bodin | A41B 13/06 |
| | | | 2/270 |
| 2,651,781 A * | 9/1953 | Buchholz | A41B 13/06 |
| | | | 2/69.5 |
| 2,738,512 A * | 3/1956 | Winer | A41B 13/005 |
| | | | 2/80 |
| 2,808,828 A | 10/1957 | Rubin | |
| 2,873,458 A | 2/1959 | Adamson | |
| 2,974,325 A | 3/1961 | Mango | |
| 2,992,440 A | 7/1961 | Revolt | |
| 3,146,736 A | 9/1964 | Hetrick | |
| 3,536,067 A | 10/1970 | Sternagel | |
| D224,822 S | 9/1972 | Lee, Jr. | |
| 3,789,439 A | 2/1974 | Berg | |
| D232,279 S | 8/1974 | White | |
| 3,845,513 A * | 11/1974 | Hubner | A47G 9/083 |
| | | | 2/69.5 |
| 3,853,121 A * | 12/1974 | Mizrachy | A61H 15/0078 |
| | | | 601/48 |
| 3,886,607 A | 6/1975 | Dunn | |
| D244,890 S | 7/1977 | Adams | |
| 4,302,850 A * | 12/1981 | Maeshima | A41D 27/10 |
| | | | 2/102 |
| 4,451,932 A * | 6/1984 | Wagemann | A61F 5/3784 |
| | | | 128/874 |
| 4,524,768 A * | 6/1985 | Serrao | A61F 5/3784 |
| | | | 128/873 |
| 4,532,654 A * | 8/1985 | Sigismonde | A41D 15/04 |
| | | | 2/97 |
| 4,553,485 A | 11/1985 | Lee | |
| 4,611,353 A | 9/1986 | Als et al. | |
| 4,619,270 A | 10/1986 | Margolis | |
| 4,750,223 A | 6/1988 | D'Arcy | |
| 4,802,244 A * | 2/1989 | McGrath-Saleh | A41B 13/06 |
| | | | 2/69 |
| 4,934,997 A | 6/1990 | Skakas | |
| D316,339 S | 4/1991 | Taylor | |
| 5,037,375 A | 8/1991 | Gatts | |
| D320,316 S | 10/1991 | Arnold | |
| 5,097,553 A * | 3/1992 | Boland | A61H 1/0292 |
| | | | 5/632 |
| 5,097,847 A * | 3/1992 | Mikhail | A61G 13/12 |
| | | | 128/849 |
| 5,113,875 A * | 5/1992 | Bennett | A47C 20/021 |
| | | | 5/648 |
| 5,117,522 A * | 6/1992 | Everett | A61G 7/0755 |
| | | | 5/644 |
| 5,125,123 A * | 6/1992 | Engle | A47C 20/025 |
| | | | 128/845 |
| 5,129,406 A | 7/1992 | Magnuson et al. | |
| 5,134,739 A * | 8/1992 | Gaffe | A61G 7/0755 |
| | | | 5/624 |
| 5,183,457 A | 2/1993 | Gatts et al. | |
| 5,228,155 A | 7/1993 | Shultz | |
| 5,295,490 A | 3/1994 | Dodakian | |
| 5,311,622 A | 5/1994 | Allen | |
| 5,381,569 A | 1/1995 | Church | |
| 5,384,922 A | 1/1995 | Jobe | |
| 5,385,153 A | 1/1995 | Jamieson et al. | |
| 5,398,353 A | 3/1995 | Sachathamakul | |
| 5,454,993 A * | 10/1995 | Kostich | A47C 20/021 |
| | | | 264/46.4 |
| D367,979 S | 3/1996 | Lewis | |
| 5,577,450 A | 11/1996 | Huang | |
| 5,640,717 A | 6/1997 | Ray | |
| 5,668,780 A | 9/1997 | Hsieh | |
| 5,684,460 A | 11/1997 | Scanlon | |
| 5,706,533 A | 1/1998 | Opheim | |
| 5,711,045 A | 1/1998 | Caster et al. | |
| 5,746,219 A * | 5/1998 | McConnell | A47D 15/008 |
| | | | 128/845 |
| 5,806,113 A | 9/1998 | McMahan et al. | |
| D401,454 S | 11/1998 | De Blaay | |
| 5,845,350 A | 12/1998 | Beemiller et al. | |
| 5,852,827 A | 12/1998 | Lear et al. | |
| 5,855,031 A | 1/1999 | Swift | |
| 5,881,408 A | 3/1999 | Bashista et al. | |
| 5,931,534 A | 8/1999 | Hutter | |
| D413,454 S | 9/1999 | Kasem | |
| 5,966,756 A * | 10/1999 | Cartier | A47G 9/086 |
| | | | 2/69.5 |
| D417,090 S | 11/1999 | Reynolds | |
| 5,988,742 A * | 11/1999 | Stevens | A47D 15/006 |
| | | | 2/69.5 |
| 5,997,491 A * | 12/1999 | Harris | A47C 20/021 |
| | | | 128/882 |
| D418,440 S | 1/2000 | Dallaire | |
| 6,009,576 A | 1/2000 | Gramme et al. | |
| 6,011,477 A | 1/2000 | Teodorescu et al. | |
| 6,068,566 A | 5/2000 | Kim | |
| 6,146,332 A | 11/2000 | Pinsonneault | |
| 6,148,455 A | 11/2000 | Kasem | |
| 6,155,976 A | 12/2000 | Sackner et al. | |
| 6,266,822 B1 * | 7/2001 | Joyce | A41B 13/06 |
| | | | 2/69 |
| 6,343,994 B1 | 2/2002 | Clarke | |
| 6,386,986 B1 | 5/2002 | Sonner | |
| 6,393,612 B1 | 5/2002 | Thach et al. | |
| 6,415,442 B1 | 7/2002 | Smith et al. | |
| 6,415,466 B1 * | 7/2002 | Laiso | A47G 9/02 |
| | | | 5/482 |
| 6,498,652 B1 | 12/2002 | Varshneya et al. | |
| 6,553,590 B1 * | 4/2003 | Leach | A47D 13/08 |
| | | | 5/655 |
| 6,578,218 B2 * | 6/2003 | Wassilefsky | A47C 20/021 |
| | | | 5/630 |
| 6,588,033 B1 | 7/2003 | Welsh, Jr. | |
| 6,594,834 B2 | 7/2003 | Fenty | |
| 6,634,045 B1 * | 10/2003 | DuDonis | A47C 20/021 |
| | | | 5/632 |
| 6,652,469 B2 | 11/2003 | Pinsonnault | |
| 6,662,390 B1 | 12/2003 | Berger et al. | |
| 6,725,481 B1 * | 4/2004 | Marshall | A61B 6/0421 |
| | | | 5/621 |
| 6,839,924 B2 | 1/2005 | Sims et al. | |
| 6,868,566 B2 | 3/2005 | Gatten et al. | |
| 6,907,626 B1 | 6/2005 | Welsh | |
| 6,916,249 B2 | 7/2005 | Meade | |
| 6,928,674 B2 | 8/2005 | Blackburn | |
| 6,966,069 B2 * | 11/2005 | Booth | A47G 9/066 |
| | | | 2/48 |
| 6,966,082 B2 | 11/2005 | Bloemer et al. | |
| D512,466 S | 12/2005 | White | |
| 6,978,479 B2 | 12/2005 | Thach et al. | |
| D518,942 S | 4/2006 | Dandrea | |
| 7,043,783 B2 | 5/2006 | Gatten et al. | |
| 7,076,819 B2 | 7/2006 | Trani et al. | |
| D526,133 S | 8/2006 | Song | |
| 7,100,724 B2 | 9/2006 | Haigh et al. | |
| 7,123,758 B2 | 10/2006 | Mostafavi et al. | |
| 7,150,057 B1 * | 12/2006 | Santiago | A47C 20/021 |
| | | | 5/648 |
| D536,191 S | 2/2007 | Kasem | |
| D536,550 S | 2/2007 | Kasem | |
| 7,181,789 B2 | 2/2007 | Gatten et al. | |
| 7,203,981 B1 | 4/2007 | Cowgill et al. | |
| 7,246,392 B2 | 7/2007 | Schmid et al. | |

(56) References Cited

U.S. PATENT DOCUMENTS

| | | | |
|---|---|---|---|
| D561,978 S | 2/2008 | Soulides | |
| 7,337,482 B2 | 3/2008 | Byrne et al. | |
| 7,347,806 B2 | 3/2008 | Nakano et al. | |
| 7,406,725 B2 | 8/2008 | Martin et al. | |
| 7,427,921 B2 | 9/2008 | Van | |
| 7,485,086 B2 | 2/2009 | Dickie et al. | |
| 7,587,769 B1 | 9/2009 | McDermott et al. | |
| 7,587,772 B2 | 9/2009 | Ward et al. | |
| D605,870 S | 12/2009 | Bergkvist | |
| D606,282 S | 12/2009 | Chen | |
| 7,685,657 B1 | 3/2010 | Hernandez et al. | |
| D613,091 S | 4/2010 | Taylor | |
| 7,722,118 B2 | 5/2010 | Bapst et al. | |
| D616,665 S | 6/2010 | Dumais | |
| 7,743,442 B2 | 6/2010 | Maloney et al. | |
| 7,774,875 B1 | 8/2010 | Zeidman et al. | |
| 7,785,257 B2 | 8/2010 | Mack et al. | |
| 7,857,677 B2 | 12/2010 | Kamm | |
| 7,918,505 B2 | 4/2011 | King et al. | |
| D640,483 S | 6/2011 | Daley et al. | |
| 7,954,187 B1 * | 6/2011 | Earnest | A61F 5/3723 5/482 |
| D644,413 S | 9/2011 | Keall | |
| 8,011,037 B1 | 9/2011 | Earnest et al. | |
| 8,032,958 B2 | 10/2011 | Pieta et al. | |
| D650,153 S | 12/2011 | Chopak et al. | |
| 8,083,601 B2 | 12/2011 | Speedie et al. | |
| 8,096,960 B2 | 1/2012 | Loree et al. | |
| 8,112,835 B2 | 2/2012 | Eirich et al. | |
| 8,141,186 B2 | 3/2012 | Jackson et al. | |
| 8,191,188 B2 | 6/2012 | Kaplan et al. | |
| 8,197,005 B2 | 6/2012 | Hopke et al. | |
| 8,225,422 B1 * | 7/2012 | McSparron | A41B 13/005 2/67 |
| 8,239,984 B2 | 8/2012 | Hopke et al. | |
| 8,269,625 B2 | 9/2012 | Hoy et al. | |
| D669,659 S | 10/2012 | Barski | |
| 8,302,225 B1 | 11/2012 | Earnest et al. | |
| 8,321,980 B2 | 12/2012 | Maloney et al. | |
| D674,614 S | 1/2013 | Morand | |
| 8,347,432 B2 | 1/2013 | Schmid et al. | |
| 8,365,325 B2 | 2/2013 | Schneider et al. | |
| 8,375,486 B2 | 2/2013 | Earnest et al. | |
| D678,693 S | 3/2013 | Bergkvist | |
| 8,395,510 B1 | 3/2013 | Kirk | |
| 8,398,538 B2 | 3/2013 | Dothie et al. | |
| 8,429,771 B2 | 4/2013 | Long et al. | |
| 8,522,375 B2 | 9/2013 | Conrad et al. | |
| 8,539,620 B1 | 9/2013 | Wynh et al. | |
| D692,209 S | 10/2013 | Dragu | |
| 8,555,414 B2 | 10/2013 | Davis et al. | |
| 8,561,227 B2 | 10/2013 | Jenkins et al. | |
| D696,486 S | 12/2013 | Barski | |
| 8,607,364 B2 | 12/2013 | Barski et al. | |
| 8,607,366 B2 | 12/2013 | Austin | |
| 8,650,663 B2 * | 2/2014 | Fair | A47G 9/068 2/69.5 |
| 8,661,582 B2 | 3/2014 | Sclare et al. | |
| 8,667,631 B2 | 3/2014 | Coates et al. | |
| 8,695,133 B2 | 4/2014 | Christensen et al. | |
| 8,726,437 B2 * | 5/2014 | Hardesty | A47D 13/08 5/655 |
| 8,745,794 B1 | 6/2014 | McDermott | |
| 8,756,731 B1 | 6/2014 | Huttner et al. | |
| 8,769,737 B1 * | 7/2014 | Duggins | A47D 7/00 5/93.1 |
| 8,776,265 B2 * | 7/2014 | Neveu | A47G 9/068 2/69.5 |
| 8,777,311 B1 | 7/2014 | Laurel et al. | |
| 8,782,831 B2 | 7/2014 | Houston et al. | |
| 8,784,227 B2 | 7/2014 | Speedie et al. | |
| 8,827,366 B2 | 9/2014 | Daley et al. | |
| 8,832,880 B2 | 9/2014 | Sheard et al. | |
| 8,845,440 B2 | 9/2014 | Hayt et al. | |
| D715,027 S | 10/2014 | Daugherty | |
| 8,863,329 B2 * | 10/2014 | Gangan | A41B 13/06 5/494 |
| D718,017 S | 11/2014 | Barski | |
| 8,898,833 B2 | 12/2014 | Coates et al. | |
| 8,904,580 B1 | 12/2014 | Christensen et al. | |
| 8,910,332 B2 | 12/2014 | Buckson | |
| 8,942,783 B2 | 1/2015 | Cervantes et al. | |
| 8,943,615 B2 * | 2/2015 | Howard | A41D 11/00 2/111 |
| 8,943,625 B2 | 2/2015 | Gotel et al. | |
| 9,003,564 B2 | 4/2015 | Wynh | |
| 9,020,622 B2 | 4/2015 | Shoham et al. | |
| D728,198 S | 5/2015 | Barski | |
| D728,199 S | 5/2015 | Barski | |
| 9,032,963 B2 | 5/2015 | Grissom | |
| D734,592 S | 7/2015 | Castillo et al. | |
| 9,119,423 B2 | 9/2015 | Gotel et al. | |
| 9,131,734 B2 | 9/2015 | Daugherty et al. | |
| D741,046 S | 10/2015 | Pelekanou | |
| 9,155,403 B2 | 10/2015 | Mountz et al. | |
| D742,097 S | 11/2015 | Dunn | |
| 9,179,711 B2 * | 11/2015 | Krawchuk | A61F 5/37 |
| D751,847 S | 3/2016 | Brown | |
| 9,332,791 B1 | 5/2016 | Bush et al. | |
| D780,472 S | 3/2017 | Behar | |
| 9,962,012 B1 | 5/2018 | Schmid et al. | |
| D825,219 S | 8/2018 | Karp et al. | |
| 10,499,696 B2 * | 12/2019 | Mitchell | A41D 23/00 |
| 11,058,160 B2 * | 7/2021 | Kwak | A41D 27/20 |
| 11,147,319 B2 * | 10/2021 | Karp | A47D 15/008 |
| 2002/0016991 A1 | 2/2002 | Brown | |
| 2002/0100116 A1 | 8/2002 | Richards et al. | |
| 2003/0208846 A1 * | 11/2003 | Guarino | A47C 20/026 5/636 |
| 2004/0070254 A1 | 4/2004 | Conlon et al. | |
| 2004/0078895 A1 | 4/2004 | Eiling et al. | |
| 2005/0022284 A1 | 2/2005 | Thach | |
| 2005/0091743 A1 | 5/2005 | Bloemer et al. | |
| 2005/0120459 A1 | 6/2005 | McConnell et al. | |
| 2005/0210592 A1 | 9/2005 | Littlehorn et al. | |
| 2005/0283908 A1 | 12/2005 | Wong et al. | |
| 2006/0025226 A1 | 2/2006 | Nakano et al. | |
| 2006/0042013 A1 | 3/2006 | Madsen | |
| 2006/0084514 A1 | 4/2006 | Speedie et al. | |
| 2006/0096031 A1 * | 5/2006 | Foster | A47D 15/008 5/655 |
| 2006/0225206 A1 | 10/2006 | Kasem | |
| 2007/0056109 A1 | 3/2007 | Forshpan et al. | |
| 2007/0060015 A1 | 3/2007 | Glatt et al. | |
| 2007/0061968 A1 | 3/2007 | Fader | |
| 2007/0085695 A1 | 4/2007 | Nerurkar et al. | |
| 2007/0111809 A1 | 5/2007 | Bellows et al. | |
| 2007/0267904 A1 | 11/2007 | Clapper et al. | |
| 2008/0005825 A1 * | 1/2008 | Tronvold | A41D 13/01 2/95 |
| 2008/0077020 A1 | 3/2008 | Young et al. | |
| 2008/0136236 A1 | 6/2008 | Kincaid et al. | |
| 2008/0196164 A1 | 8/2008 | Caliiung | |
| 2008/0217150 A1 | 9/2008 | Chen | |
| 2008/0314665 A1 | 12/2008 | Sanders et al. | |
| 2009/0062622 A1 | 3/2009 | Lin et al. | |
| 2009/0064390 A1 | 3/2009 | Beiring et al. | |
| 2009/0070914 A1 * | 3/2009 | Landeck | A41D 1/04 2/95 |
| 2009/0131185 A1 | 5/2009 | Speedie | |
| 2009/0206642 A1 | 8/2009 | Raphael et al. | |
| 2010/0044164 A1 | 2/2010 | Thorne | |
| 2010/0201171 A1 | 8/2010 | Velderman et al. | |
| 2010/0218299 A1 | 9/2010 | Damir | |
| 2010/0228315 A1 | 9/2010 | Nielsen | |
| 2010/0231421 A1 | 9/2010 | Rawls-Meehan | |
| 2010/0253504 A1 | 10/2010 | Lliteras et al. | |
| 2010/0257654 A1 | 10/2010 | Waters et al. | |
| 2010/0275373 A1 | 11/2010 | Kaplan | |
| 2010/0298742 A1 | 11/2010 | Perlman | |
| 2010/0328075 A1 | 12/2010 | Rahamim et al. | |
| 2011/0025915 A1 | 2/2011 | Daban et al. | |
| 2011/0032103 A1 | 2/2011 | Bhat et al. | |

(56) References Cited

U.S. PATENT DOCUMENTS

| | | |
|---|---|---|
| 2011/0078855 A1 | 4/2011 | Buckson et al. |
| 2011/0099719 A1 | 5/2011 | Hardesty et al. |
| 2011/0113549 A1 | 5/2011 | Riddiford et al. |
| 2011/0179546 A1 | 7/2011 | Millette et al. |
| 2011/0277210 A1 | 11/2011 | Hardesty et al. |
| 2011/0308011 A1 | 12/2011 | Cheng |
| 2012/0025992 A1 | 2/2012 | Tallent et al. |
| 2012/0054967 A1* | 3/2012 | Rieber .................. A47C 16/02 5/648 |
| 2012/0083670 A1 | 4/2012 | Rotondo |
| 2012/0125347 A1 | 5/2012 | Soileau et al. |
| 2012/0216349 A1 | 8/2012 | Kaplan et al. |
| 2012/0284922 A1 | 11/2012 | Gangan et al. |
| 2012/0297518 A1 | 11/2012 | Aiken et al. |
| 2012/0311762 A1 | 12/2012 | Aiken et al. |
| 2013/0123654 A1 | 5/2013 | Rahamim et al. |
| 2013/0139290 A1 | 6/2013 | Barski et al. |
| 2013/0165809 A1 | 6/2013 | Abir |
| 2013/0185867 A1 | 7/2013 | Long et al. |
| 2014/0059762 A1 | 3/2014 | Bonczek |
| 2014/0068834 A1 | 3/2014 | Skinner |
| 2014/0130254 A1 | 5/2014 | Jeong |
| 2014/0173822 A1 | 6/2014 | Doering et al. |
| 2014/0249382 A1 | 9/2014 | Bhat et al. |
| 2014/0250558 A1 | 9/2014 | Russo |
| 2014/0250592 A1 | 9/2014 | Karp et al. |
| 2014/0265480 A1 | 9/2014 | Perrin et al. |
| 2014/0339867 A1 | 11/2014 | Daley et al. |
| 2014/0345042 A1 | 11/2014 | Morand |
| 2015/0026886 A1 | 1/2015 | Gangan |
| 2015/0045608 A1 | 2/2015 | Karp et al. |
| 2015/0059089 A1 | 3/2015 | Falkiner |
| 2015/0089712 A1* | 4/2015 | Gamble .................. A41D 3/08 2/88 |
| 2015/0101100 A1* | 4/2015 | Flowers ................ A41B 13/06 2/69.5 |
| 2015/0126819 A1 | 5/2015 | Cervantes |
| 2015/0196137 A1 | 7/2015 | Zhao et al. |
| 2015/0250330 A1 | 9/2015 | Mountz et al. |
| 2015/0250419 A1 | 9/2015 | Cooper et al. |
| 2016/0095776 A1* | 4/2016 | Batiste ................ A61G 7/0755 5/648 |
| 2016/0128392 A1 | 5/2016 | Krawchuk |
| 2016/0165961 A1 | 6/2016 | Karp |
| 2016/0166081 A1 | 6/2016 | Karp et al. |
| 2016/0174619 A1 | 6/2016 | Waters |
| 2016/0174728 A1 | 6/2016 | Karp et al. |
| 2016/0278443 A1* | 9/2016 | Clements ............. A41B 13/065 |
| 2016/0310067 A1 | 10/2016 | Heinrich et al. |
| 2017/0043117 A1 | 2/2017 | Karp et al. |
| 2017/0043118 A1 | 2/2017 | Karp et al. |
| 2018/0007976 A1* | 1/2018 | Lager .................. A47D 15/008 |
| 2019/0223517 A1* | 7/2019 | Collins ............. A41D 13/1272 |
| 2019/0254355 A1* | 8/2019 | Griffin .................. A41D 27/20 |
| 2020/0138137 A1* | 5/2020 | Eckensweiler ....... A41F 19/005 |
| 2020/0196685 A1* | 6/2020 | Williams ................ A47G 9/04 |
| 2021/0059319 A1* | 3/2021 | Karp .................... A41B 13/065 |
| 2021/0138184 A1* | 5/2021 | Lois ..................... A61M 21/02 |
| 2021/0259329 A1* | 8/2021 | Kiik-Miley ............ A41B 13/00 |

FOREIGN PATENT DOCUMENTS

| | | | |
|---|---|---|---|
| CA | 2459037 | 8/2005 | |
| CA | 2760609 | 11/2010 | |
| CA | 2848529 | 3/2013 | |
| CA | 2918029 | 4/2016 | |
| CN | 1701732 A | 11/2005 | |
| CN | 1759897 A | 4/2006 | |
| CN | 101036556 A | 9/2007 | |
| CN | 201042329 A | 4/2008 | |
| CN | 201085348 Y | 7/2008 | |
| CN | 101756556 A | 6/2010 | |
| CN | 201664114 U | 12/2010 | |
| CN | 201718870 U | 1/2011 | |
| CN | 102727004 A | 10/2012 | |
| DE | 102008059469 A1 * | 6/2009 | ......... A41D 13/1272 |
| EP | 0617907 | 6/1997 | |
| EP | 1748711 | 2/2007 | |
| EP | 2617329 | 7/2013 | |
| EP | 2197322 | 2/2014 | |
| EP | 2292124 | 7/2014 | |
| EP | 2915459 | 9/2015 | |
| EP | 292812 | 10/2015 | |
| EP | 2756136 | 8/2016 | |
| FR | 2580162 A1 * | 10/1986 | ............. A47G 9/086 |
| FR | 2669201 | 5/1992 | |
| GB | 388685 A * | 3/1933 | ........... A47D 15/008 |
| GB | 1588724 A * | 4/1981 | ............. A47G 9/083 |
| GB | 2312374 | 10/1997 | |
| JP | 07275091 | 10/1995 | |
| JP | 07289394 | 11/1995 | |
| JP | 2000510022 | 8/2000 | |
| KR | 1020040097883 | 11/2004 | |
| KR | 1020060019024 | 3/2006 | |
| KR | 1020060079587 | 7/2006 | |
| KR | 20090121797 A | 11/2009 | |
| NO | 2013038248 | 3/2013 | |
| NO | 2016055946 | 4/2016 | |
| WO | 199817150 A2 | 4/1998 | |
| WO | 2007062499 | 6/2007 | |
| WO | 2010098702 | 9/2010 | |
| WO | 2010127299 | 11/2010 | |
| WO | 2013059625 | 4/2013 | |
| WO | 2013087955 | 6/2013 | |
| WO | 2013135975 | 9/2013 | |
| WO | 2013188810 | 12/2013 | |
| WO | 2014078442 | 5/2014 | |
| WO | 2015017709 | 2/2015 | |
| WO | 2015078937 A1 | 6/2015 | |
| WO | 2015143430 | 9/2015 | |
| WO | 2016096518 | 6/2016 | |
| WO | 2016123619 | 8/2016 | |
| WO | 2016138441 | 9/2016 | |

OTHER PUBLICATIONS

SNOO Bassinet, Can this High-Tech Bassinet Keep Sleep-Deprived Parents Sane?, The Wall Street Journal, http://www.wsj.com/articles/can-thls-high-tech-bassinet-keep-sleep-deprived-parents-sane, Oct. 18, 2018.

Office Action issued in Australian Application No. 2012325947, dated Aug. 22, 2016.

Office Action issued in Mexican Patent Application No. MX/a/2014/004648, dated Mar. 24, 2017.

Extended European search report issued in European Patent Application No. 14831425.5, dated Feb. 24, 2017.

Putting Baby in SNOO Sack, https://www.youtube.com/watch?v=NvTIOzWxG80, Oct. 28, 2016.

About SUID and SIDS, Centers for Disease Control and Prevention, http://www.cdc.gov/sids/aboutsuidandsids.htm, Oct. 3, 2016, (accessed Nov. 3, 2016), 2 pages.

Infant Sleep Forum Posting, http://www.sleepnet.com/ infant/messages/501.html, (accessed Mar. 16, 2015), 2 pages.

Safety Standard for Bassinets and Cradles; Correction, Federal Register, vol. 78, No. 247, https://www.bderalregistergov/documents/2013/12/24/2013-30527/safety-standard-for-bassinets-and-cradles-correction (accessed Nov. 10, 2016), Consumer Product Safety Commission, Dec. 24, 2013, 1 page.

Safety Standard for Bassinets and Cradles; Correction, Federal Register, vol. 78, No. 205, https://www.bderalregistergov/documents/2013/10/23/2013-24203/safety-standard-for-bassinets-and-cradles (accessed Nov. 10, 2016), Consumer Product Safety Commission, Oct. 23, 2013, 18 pages.

Safety Standard for Bedside Sleepers, Federal Register, vol. 79, No. 10, https://www.federalregister.gov/documents/2014/01/15/2014-00597/safety-standard-for-bedside-sleepers, (accessed Nov. 10, 2016), Consumer Product Safety Commission, Jan. 15, 2014, 9 pages.

EP Application No. 12781007.5, Examination Notification Art. 94(3) mailed May 5, 2015, Unacuna, LLC, 3 Pages.

(56) References Cited

OTHER PUBLICATIONS

AAP Task Force On SIDS, The Changing Concept of Sudden Infant Death Syndrome: Diagnostic Coding Shifts, Controversies Regarding the Sleeping Environment, and New Variables to Consider in Reducing Risk, Peds, vol. 116, 2005, pp. 1245-1255.
Ariagno, et al., Fewer spontaneous arousals during prone sleep in preterm infants at 1 and 3 months corrected age, Journal of Perinatology, vol. 26, 2006, pp. 306-312.
Carpenter, et al., Sudden unexplained infant death in 20 regions in Europe: case control study, The Lancet, vol. 363, No. 9404, 2004, pp. 185-191.
Colvin, et al., Sleep Environment Risks for Younger and Older Infants, Pediatrics, vol. 134, Jul. 2014, pp. e406-e412.
Galland, et al., Prone versus supine sleep position: a review of the physiological studies in SIDS research, J Paediatr Child Health, vol. 38, No. 4, Aug. 2002, pp. 332-338.
Groswasser, et al., Reduced arousals following obstructive apneas in infants sleeping prone, Pediatric Research, vol. 49, No. 3, 2001, pp. 402-406.
Horne, et al., Effects of body position on sleep and arousal characteristics in infants, Early Human Development, vol. 69, iss. 1-2, Oct. 2002, pp. 25-33.
Horne, et al., The prone sleeping position impairs arousability in term infants, The Journal of Pediatrics, vol. 138, No. 6, 2001, pp. 811-816.
Kato, et al., Spontaneous Arousability in Prone and Supine Position in Healthy Infants, Sleep, vol. 29, No. 6, 2006, pp. 785-790.
L'Hoir, et al., Risk and preventive factors for cot death in The Netherlands, a low-incidence country, Eur J Pediatr, fol. 157, 1998, pp. 681-688.
Li et al., Infant Sleeping Position and the Risk of Sudden Infant Death Syndrome in California, 1997-2000, Am J Epidemiol, vol. 157, No. 5, 2003, pp. 446-455.
McDonnell, et al., Infant Deaths and Injuries Associated with Wearable Blankets, Swaddle Wraps, and Swaddling, J. Pediatr., vol. 164, No. 5, May 2014, pp. 1152-1156.
Mitchell, et al., Changing Infants' Sleep Position Increases Risk of Sudden Infant Death Syndrome, Arch Ped Adol Med., vol. 153, 1999, pp. 1136-1141.
Oyen, et al., Combined effects of sleeping position and prenatal risk factors in sudden infant death syndrome: the Nordic Epidemiological SIDS Study, Pediatrics, vol. 100, No. 4, 1997, pp. 613-621.
International Preliminary Report On Patentability With Written Opinion for PCT/US2012/061069, dated May 1, 2014.
International Search Report and Written Opinion for PCT/US2012/061069, dated Mar. 11, 2012.
International Preliminary Reporton Patentability for PCT/US2014/049253, dated Feb. 11, 2016.
International Search Report and Written Opinion for PCT/US2014/049253, dated Nov. 24, 2014.
International Search Report and Written Opinion for PCT/US2016/019878. dated May 6, 2016.
Pease, et al., Swaddling and the Risk of Sudden Infant Death Syndrome: A Meta-analysis, Pediatrics, vol. 137, No. 3, Jun. 2016, pp. e20153275 (11 pages).
Ponsonby, et al., Factors potentiating the risk of Sudden Infant Death Syndrome associated with the Prone Position, NEJM, vol. 329, 1993, pp. 377-382.
Shapiro-Mendoza, et al., Trends in Infant Bedding Use: National Infant Sleep Position Study, 1993-2010, Pediatrics, vol. 135, 2015, pp. 10-17.
Tuladhar, et al., Effects of sleep position, sleep state and age on heart rate responses following provoked arousal n term infants, Early human development, vol. 71, iss. 2, Apr. 2003, pp. 157-169.
Vennemann, et al., Sleep Environment Risk Factors for Sudden Infant Death Syndrome: The German Sudden Infant Death Syndrome Study, Pediatrics, vol. 123, No. 4, Apr. 2009, pp. 1162-1170.
International Search Report and Written Opinion for PCT/US2019/019010, dated May 24, 2019.
International Search Report and Written Opinion for PCT/US2017/057055, dated Feb. 1, 2018.
Naver blog, URL: https://blog.naver.com/redtony02/30103163614.
SIDS and Other Sleep-Related Infant Deaths: Expansion of Recommendations for a Safe Infant Sleeping Environment, Task Force on Sudden Infant Death Syndrome, Pediatrics, 2011; 128:1030 (Oct. 17, 2011).
Office Action issued in CN 2019800146663 with English translation, dated Dec. 29, 2021.
Extended European Search Report, EP 19757210.0, dated Feb. 11, 2022.

* cited by examiner

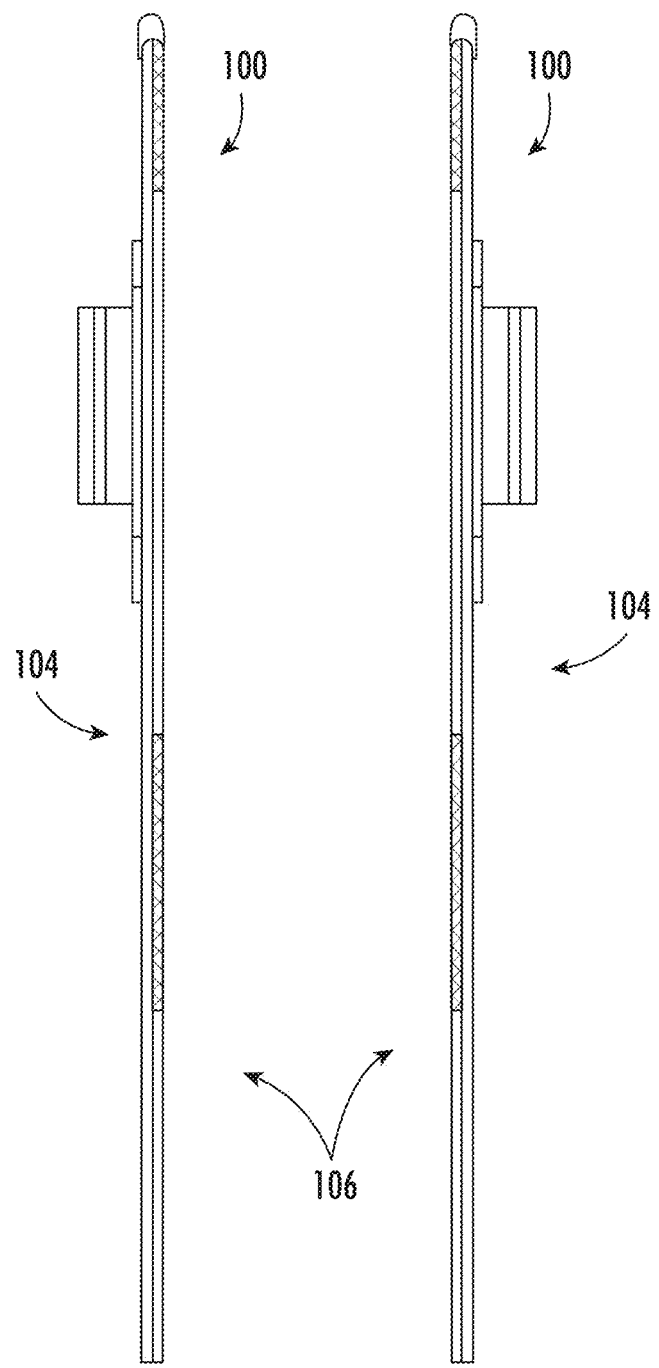

INFANT SLEEP GARMENT

CROSS-REFERENCE TO RELATED APPLICATIONS

The present application claims the benefit of U.S. Provisional Patent No. 62/633,529, filed Feb. 21, 2018. U.S. Provisional Patent No. 62/633,529 is hereby incorporated by reference herein in its entirety.

TECHNOLOGY FIELD

The present disclosure relates to infant garments, and specifically to garments with infant calming and sleep-aid properties intended to assist in triggering a calming reflex in an infant.

BACKGROUND

Persistent crying and poor infant sleep are perennial and ubiquitous causes of parent frustration. During the first months of life, babies fuss/cry an average of about two hours/day and wake two to three times a night. One in six infants is brought to a medical professional for evaluation for sleep/cry issues.

Infant crying and parental exhaustion are often demoralizing and directly linked to marital conflict, anger towards the baby, impaired job performance, and are primary triggers for a cascade of serious/fatal health sequelae, including postpartum depression (which affects about 15% of all mothers and 25-50% of their partners), breastfeeding failure, child abuse and neglect, infanticide, suicide, unsafe sleeping practices, SIDS/suffocation, cigarette smoking, excessive doctor visits, overtreatment of infants with medication, automobile accidents, dysfunctional bonding, and perhaps maternal and infant obesity. Thus, there is a need for improved sleep aids to promote sleep (by reducing sleep latency and increasing sleep efficiency). "Sleep latency" may be defined as the length of time between going to bed and falling asleep. "Sleep efficiency" may be defined as the ratio of time spent asleep (total sleep time) to the amount of time spent in bed.

SUMMARY

In one aspect, an infant sleep garment comprises an enclosure having a first side and a second side. The first side and the second side may together define an enclosure volume therebetween. The enclosure may include a first portion, a second portion, a weight element, and a support element. The first portion may be configured to accommodate at least a portion of a lower body of an infant within the enclosure volume when the infant is enclosed therein. The second portion may be located in a superior position relative to the first portion and be configured to accommodate at least a portion of an upper body of the infant within the enclosure volume when the infant enclosed therein. The weight element may be coupled or couplable to the first side along the second portion at a location corresponding to an abdominal or chest area of the infant when the infant is enclosed within the enclosure volume. The support element may be coupled or couplable to the second side along the first portion at a location corresponding to at least a portion of the lower body of the infant when the infant is enclosed within the enclosure volume. The support element may be configured to elevate hips and feet of the infant relative to the at least a portion of the upper body of the infant.

In one embodiment, the weight element weighs between 0.5 pounds and 1.5 pounds and the support element includes an arcuate shaped cross-section that extends a distance into the enclosure volume at least 4 inches.

In another aspect, an infant sleep garment includes an enclosure having a first side and a second side. The first side and the second side may together define an enclosure volume therebetween. The enclosure may include a first portion and a second portion. The first portion may be configured to accommodate at least a portion of a lower body of an infant within the enclosure volume when the infant is enclosed therein. The second portion may be located in a superior position relative to the first portion and may be configured to accommodate at least a portion of an upper body of the infant within the enclosure volume when the infant is enclosed therein. The first side may be configured to couple with a weight element along the second portion. The second side may be configured to couple with a support element along the first portion. When coupled with the first side, the weight element may be positioned to apply weight to at least a portion of the upper body of the infant. When coupled with the second side, the support element may be positioned to support the at least a portion of the at least a portion of the lower body of the infant to elevate hips and feet of the infant relative to the at least a portion of the upper body of the infant.

In various embodiments, the first side includes a compartment configured to receive the weight element to thereby couple the weight at the first side. In one embodiment, the first side is configured to couple with the weight element at a location configured to position the weight over a chest or abdominal area of the infant when the infant is enclosed in the enclosure volume to apply pressure to the same when the weight element is received therein. In one example, the weight element weighs between 0.5 and 1.5 pounds.

In some embodiments, the second side includes a compartment configured to receive the support element. The compartment may be configured to receive the support element and be positioned at a location along the second side corresponding to at least thighs and feet of the infant to underlay the same when the infant is enclosed within the enclosure volume. In one embodiment, the compartment configured to receive the support element is positioned at a location along the second side corresponding to at least hips of the infant to underlay the same when the infant is enclosed within the enclosure volume.

In various embodiments, when coupled at the second side, the support element extends 4.5 to 5.5 inches into the enclosure volume. In one example, the support element includes a cylindrical portion that when coupled at the second side extends into the enclosure volume. In a further example, when coupled at the second side, an arcuate shaped cross-section portion of the support element may extend a distance greater than 4 inches or between 4.5 to 5.5 inches into the enclosure volume.

In an embodiment, the first side and the second side are selectively couplable along their respective lateral peripheries extending between the first and second portions. Adjacent lateral peripheries of the first and second sides may include attachment members configured to couple the adjacent lateral peripheries. In one example, the attachment members comprise zipper halves that are matable with adjacent zipper to couple the lateral peripheries.

In some embodiments, the first and second sides may be configured to accommodate an infant sleep sack within the enclosure volume. In one example, the enclosure includes laterally positioned openings to accommodate passage of a sleep sack securing mechanism from the enclosure volume to an exterior of the enclosure for attachment to a moveable sleep platform to thereby indirectly fix the enclosure to movement of the sleep platform.

In one embodiment, the first side includes a compartment configured to receive the weight element to thereby couple the weight at the first side and the second side includes a compartment configured to receive the support element. The compartment configured to receive the weight element may be positioned along the first side at a location corresponding to a chest or abdominal area of the infant when the infant is enclosed within the enclosure volume such that the weight element when received therein applies pressure to the same. The compartment configured to receive the support element may be positioned along the second side at a location to underlay the lower body of the infant when the infant is enclosed within the enclosure volume. When received within the compartment, the support element may extend a distance into the enclosure volume a distance greater than 4 inches or between 4.5 to 5.5 inches.

In still another aspect, an infant sleep garment comprises an enclosure having a first side and a second side. The first side and the second side may together define an enclosure volume therebetween. The enclosure may include a first portion, a second portion. The first portion may be configured to accommodate at least a portion of a lower body of an infant within the enclosure volume when the infant is enclosed therein. The second portion may be located in a superior position relative to the first portion and be configured to accommodate at least a portion of an upper body of the infant within the enclosure volume when the infant enclosed therein. The enclosure may further include a weight element, a support element, or both. The weight element may be coupled or couplable to the first side along the second portion at a location corresponding to an abdominal or chest area of the infant when the infant is enclosed within the enclosure volume. The support element may be coupled or couplable to the second side along the first portion at a location corresponding to at least a portion of the lower body of the infant when the infant is enclosed within the enclosure volume. The support element may be configured to elevate hips and feet of the infant relative to the at least a portion of the upper body of the infant.

In one embodiment, the weight element weighs between 0.5 pounds and 1.5 pounds and the support element includes an arcuate shaped cross-section that extends a distance into the enclosure volume at least 4 inches.

In still another aspect, an embodiment of the present disclosure includes an infant sleep garment comprising a body having a first side, and a second side opposite the first side, the first and second sides defining an internal volume therebetween, the internal volume comprising: a first portion configured to accommodate at least a portion of an infant's lower body; and a second portion located in a superior position relative to the first portion and configured to accommodate at least a portion of the infant's upper body.

In an embodiment, the sleep garment may further comprise a first accommodation mechanism connected to the body for receiving a support element, the first accommodation mechanism being located proximate to and inferior relative to the first portion at the second side, and wherein the support element, upon being received at the first accommodation mechanism, is configured to support the infant's legs at an elevated angle relative to the infant's hips.

In an embodiment, the sleep garment may further comprise a first securing mechanism; wherein the first securing mechanism is connected to the body and configured to fix the sleep garment to a sleep surface;

In an embodiment, a surface of the support element may be inclined upwardly or downwardly from a proximal end to a distal end. In an embodiment, the surface of the support element may be level, partial inclined, or shaped to have any geometries that may allow the infant to rest in a comfortable position.

In an embodiment, the support element may comprise a flat portion and an inclined portion, the inclined portion further comprising the inclined surface.

In an embodiment, the first side may comprise a first coupling mechanism coincident with the sagittal plane of the infant and allowing access to the internal volume In an embodiment, a portion of the body may comprise a mesh fabric for allowing air to move therethrough.

In an embodiment, the elevated angle relative to the infant's hips may be between 30 and 160 degrees.

In an embodiment, the support element, upon being received at the first accommodation mechanism, may be located outside the interior volume.

In an embodiment, the support element, upon being received at the first accommodation mechanism, may be located inside the interior volume.

In an embodiment, the infant sleep garment may further comprise a second securing mechanism. The second securing mechanism may be attached to the body and configured to fix an infant within the interior volume.

In an embodiment, the infant sleep garment may further comprise a second attachment mechanism. The second attachment mechanism may be configured to receive a weight element at a location proximate to the second portion at the first side of the body, thereby applying pressure to the infant's body.

In an embodiment, the second attachment mechanism may be connected to the body at the location proximate to the second portion at the first side of the body.

In an embodiment, the weight element may weigh between 1 ounce and 3 pounds.

In an embodiment, the infant sleep garment may further comprise a first accommodation mechanism connected to a sleep surface for receiving a support element, the first accommodation mechanism being located proximate to and inferior relative to the first portion at the second side; wherein the support element, upon being received at the first accommodation mechanism, may be configured to support the infant's legs at an elevated angle relative to the infant's hips.

In an embodiment of the present disclosure, an infant sleep garment may further comprise: a second attachment mechanism connected to the body. The second accommodation mechanism may be configured to receive a weight element at a location proximate to the second portion at the first side of the body, thereby applying pressure to the infant's body.

In an embodiment, the sleep garment may further comprise an outer enclosure configured to accommodate a portion of the body therein.

In an embodiment, the sleep garment may further comprise a first accommodation mechanism connected to the outer enclosure for receiving a support element, the first accommodation mechanism being located proximate to and inferior relative to the first portion at the second side; wherein the support element, upon being received at the first accommodation mechanism, may be configured to support the infant's legs at an elevated angle relative to the infant's hips.

In an embodiment, the outer enclosure may comprise a second coupling mechanism extending partially around the periphery of the outer enclosure and allowing accommodation of the body therein.

In an embodiment, a portion of the outer enclosure may comprise a mesh fabric for allowing air to move therethrough.

In an embodiment, the sleep garment may be configured to receive a weight element at a location proximate to the second portion at the first side of the body, thereby applying pressure to the infant's body.

In an embodiment, the second portion of the internal volume may comprise a compartment to receive the weight element at the location proximate to the second portion at the first side of the body.

In an embodiment, the weight element may be received at the location proximate to the second portion at the first side of the body by connecting the weight element to the second portion.

In an embodiment, the sleep garment may be configured to receive a weight element at a location proximate to the second portion at the first side of the body, thereby applying pressure to the infant's body; and the outer enclosure further may comprise a second compartment for accommodating the weight element at the location proximate to the second portion at the first side of the body.

In an embodiment, the weight element may be received at the location proximate to the second portion at the first side of the body by connecting the weight element to the second portion.

In an embodiment, the second portion of the internal volume may comprise a compartment to receive the weight element at the location proximate to the second portion at the first side of the body.

In another aspect of the present disclosure, an enclosure for accommodating an infant may comprise: a first side and a second side opposite the first side; a first portion configured to accommodate an infant's legs between the first and second sides; a second portion for accommodating the infant's torso beneath the first side; wherein the first portion may comprise a first accommodation mechanism for receiving a support element configured to support the infant's legs at an elevated angle relative to the infant's hips; and wherein the second portion may comprise a second accommodation mechanism for receiving a weight element configured to apply pressure to the infant's body.

In an embodiment, portions of the first and second side may comprise a mesh fabric for allowing air to move therethrough.

In an embodiment, the first and second side may be at least partially connected by a coupling mechanism extending partially around the periphery of the first portion.

In an embodiment, the first accommodation mechanism may comprise a compartment for receiving the support element therein.

In an embodiment, the second accommodation mechanism may comprise a compartment for receiving the weight element therein.

In an embodiment, the first and second sides may be configured to at least partially accommodate an infant sleep garment therebetween.

In one aspect, an infant sleep garment comprises: a sleep sack. The sleep sack may comprise: a body defining an interior volume configured to enclose an infant therein; and a securing mechanism configured to secure the sleep sack on a sleep surface, the securing mechanism comprising a first expanse of material connected to the body and extending outwardly from a first lateral side of the body, and a second expanse of material extending from a second lateral side of the body; and an enclosure having a first side and a second side, the first side and the second side together defining an enclosure volume therebetween configured to receive the sleep sack, wherein the enclosure comprises: a first portion configured to accommodate a portion of the sleep sack within the enclosure volume that corresponds to least a portion of a lower body of an infant when the infant is enclosed within the sleep sack; a second portion located in a superior position relative to the first portion and configured to accommodate a portion of the sleep sack corresponding to at least a portion of an upper body of the infant when the infant is enclosed within the sleep sack; a weight element coupled or couplable to the first side along the second portion; a support element coupled or couplable to the second side along the first portion at a location corresponding to at least a portion of the lower body of the infant when the infant is enclosed within the enclosure volume, wherein the support element is configured to elevate legs and feet of the infant relative to the at least a portion of the upper body of the infant; and first and second lateral sides, wherein the first lateral side includes a first opening that is positioned at a location corresponding to the first expanse of material when the sleep sack is received within the enclosure volume and the second lateral side includes a second opening that is positioned at a location corresponding to the second expanse of material when the sleep sack is received within the enclosure volume, and wherein the first opening and the second opening are configured to provide a passage through which the respective first and second expanses of material may be extended to an exterior side of the enclosure from the enclosure volume to secure the sleep sack on the sleep surface while received within the enclosure volume.

In one aspect, an infant sleep garment comprises: a sleep sack. The sleep sack may comprise: a body defining an interior volume configured to enclose an infant therein; and a securing mechanism configured to secure the sleep sack on a sleep surface, the securing mechanism comprising a first expanse of material connected to the body and extending outwardly from a first lateral side of the body, and a second expanse of material extending from a second lateral side of the body; and an enclosure having a first side and a second side, the first side and the second side together defining an enclosure volume therebetween configured to receive the sleep sack, wherein the enclosure comprises: a first portion configured to accommodate a portion of the sleep sack within the enclosure volume that corresponds to at least a portion of a lower body of an infant when the infant is enclosed within the sleep sack; and a second portion located in a superior position relative to the first portion and configured to accommodate a portion of the sleep sack within the enclosure volume that corresponds to at least a portion of an upper body of the infant when the infant is enclosed within the sleep sack; wherein the first side is configured to couple with a weight element along the second portion to position the weight element to apply weight to at least a portion of the upper body of the infant when the sleep sack encloses the infant within the interior volume and is received within the enclosure volume, and wherein the second side is configured to couple with a support element along the first portion to position the support element under at least a portion of the at least a portion of the lower body of the infant to elevate hips and feet of the infant relative to the at least a portion of the upper body of the infant when the sleep sack encloses the infant within the interior volume and is received within the enclosure volume; and first and second lateral sides, wherein the first lateral side includes a first opening that is positioned at a location corresponding to the first expanse of material when the sleep sack is received within the enclosure volume and the second lateral side includes a second opening that is positioned at a location corresponding to the second expanse of material when the sleep sack is received within the enclosure volume, and wherein the first opening and the second opening are configured to provide a passage through which the respective first and second expanses of material may be extended to an exterior side of the enclosure from the enclosure volume to secure the sleep sack on the sleep surface while received within the enclosure volume.

In one aspect, an infant sleep garment comprises: a sleep sack. The sleep sack may comprise: a body defining an interior volume configured to enclose an infant therein; and a securing mechanism configured to secure the sleep sack on a sleep surface, the securing mechanism comprising a first expanse of material connected to the body and extending outwardly from a first lateral side of the body, and a second expanse of material extending from a second lateral side of the body; and an enclosure having a first side and a second side, the first side and the second side together defining an enclosure volume therebetween configured to receive the sleep sack, wherein the enclosure comprises: a first portion configured to accommodate a portion of the sleep sack within the enclosure volume that corresponds to at least a portion of a lower body of an infant when the infant is enclosed within the sleep sack; and a second portion located in a superior position relative to the first portion and configured to accommodate a portion of the sleep sack within the enclosure volume that corresponds to at least a portion of an upper body of the infant when the infant is enclosed within the sleep sack; first and second lateral sides, wherein the first lateral side includes a first opening that is positioned at a location corresponding to the first expanse of material when the sleep sack is received within the enclosure volume and the second lateral side includes a second opening that is positioned at a location corresponding to the second expanse of material when the sleep sack is received within the enclosure volume, and wherein the first opening and the second opening are configured to provide a passage through which the respective first and second expanses of material may be extended to an exterior side of the enclosure from the enclosure volume to secure the sleep sack on the sleep surface while received within the enclosure volume; and at least one of a weight element coupled or couplable to the first side along the second portion at a location corresponding to an abdominal or chest area of the infant when the infant is enclosed within the sleep sack and the sleep sack is received within the enclosure volume, wherein the weight element weighs between 1 pound and 1.5 pounds; or a support element configured to elevate hips and feet of the infant relative to the at least a portion of the upper body of the infant and is coupled or couplable to the second side along the first portion at a location corresponding to at least a portion of the lower body of the infant when the infant is enclosed within the sleep sack and the sleep sack is received within the enclosure volume.

BRIEF DESCRIPTION OF THE DRAWINGS

The novel features of the described embodiments are set forth with particularity in the appended claims. The described embodiments, however, both as to organization and manner of operation, may be best understood by reference to the following description, taken in conjunction with the accompanying drawings in which:

FIG. 4 is a left-to-right perspective view illustration of the left side of an infant sleep garment according to various embodiments described herein;

FIG. 5 is a right-to-left perspective view illustration of the right side of an infant sleep garment according to various embodiments described herein;

DETAILED DESCRIPTION

Figure 1:
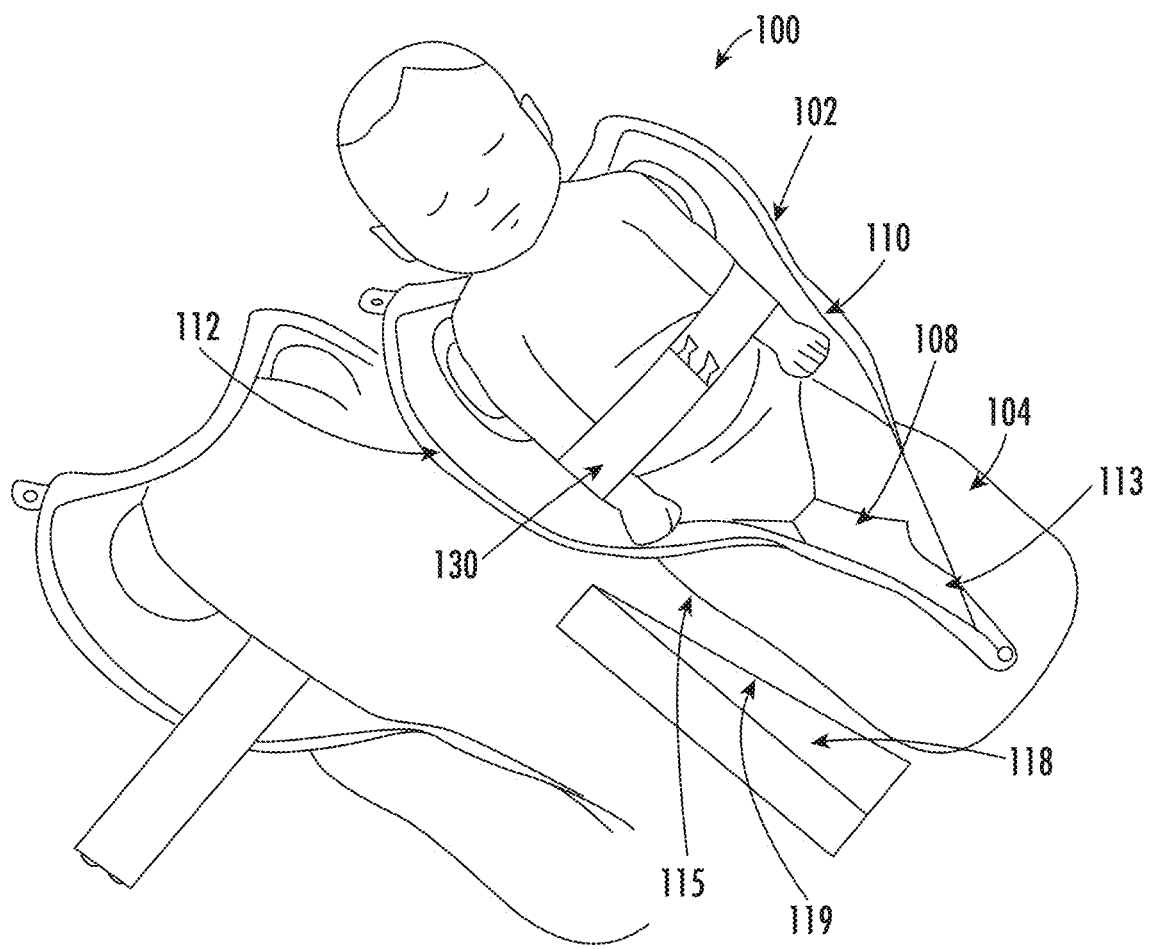
FIG. 1 is a perspective view illustration of an infant sleep garment according to various embodiments described herein.

Traditional parenting practices have utilized swaddling, rhythmic motion and certain sounds to soothe fussing infants and promote sleep by reducing sleep latency and increasing sleep efficiency.

Swaddling, rhythmic motion and certain positions and sounds may be utilized to imitate elements of in utero sensory milieu and activate a suite of subcortical reflexes, called the "calming reflex." during the first 4-6 months of a baby's life.

Swaddling, for example, is a method of snug wrapping with the arms restrained at the sides of the baby. This imitates the confinement and continual touch a baby experienced in the womb. Swaddling also inhibits startling and flailing, which often interrupts sleep and starts/exacerbates crying.

Rhythmic motions may include jiggling motions that replicate movement a baby experienced as a fetus when the mother was walking. This motion is believed to stimulate the vestibular apparatus in the inner ear. A specific rumbling noise may also be incorporated that imitates the sound created by the turbulence of the blood flowing through the uterine and umbilical arteries. In utero, the sound level a fetus hears has been measured at between 75 and 92 dB.

Like the children and adults they will grow to become, each baby is an individual that may favor a specific and/or unique mix of motion and sound that most efficiently activates his or her calming reflex. This preferred mix is believed to stay consistent through the first months of life (e.g., babies who respond best to swaddling plus jiggling continue to respond to those modalities over time and do not abruptly switch their preference to swaddling plus sound). In utero, babies are confined in a small space requiring them to flex their hips and knees with the knees pressing against the stomach and arms pressed against the chest.

The calming reflex has several constant characteristics. It is triggered by a stereotypical sensory input; produces a stereotypical behavioral output; demonstrates a threshold phenomenon (i.e. stimuli that are too mild may not be sufficient to activate a response); has a threshold that varies between individuals (i.e. is higher or lower for any given child); the threshold varies by state (e.g. fussing and crying raise the level of stimulation required to exceed threshold and bring about reflex activation); the reflex is universally present and relatively obligatory at birth, but wanes after 3-4 months of age.

In addition, crib death or SUID (Sudden Unexplained Infant Death) is a leading cause of infant mortality. Approximately 3700 US babies die each year from SUID during the first year of life. The peak occurrence is from 2-4 months of age, with 80% of the victims being under 4 months and 90% being under 6 months of age.

In the 1990's, a program to reduce SUID deaths called "Back to Sleep" was introduced. At that time, it was discovered that sleeping on the stomach was a key triggering factor in many of the deaths, so caregivers were instructed to place babies on their backs for sleeping. Within less than a decade, the rate of SUID dropped almost in half, however, since 1999, the SUID incidence has barely diminished. Studies have indicated that stomach sleeping may indeed predispose babies to SUID by causing suffocation or by reducing infant arousability and inhibiting breathing.

In addition, many babies fall out of their bassinet during the first 6 months of life. Federal reports reveal that 69% of recent bassinet/cradle incidents have been attributed to falling. All falls resulted in head injury. Alarmingly, 45% of falls occurred in infants five months old or less.

Therefore, a need exists for an infant garment that constrains the movement of the infant relative to a sleep surface while promoting the calming reflex of the infant.

In an embodiment of the present disclosure, an infant sleep garment may comprise a body having a first side, and a second side opposite the first side, the first and second sides defining an internal volume therebetween, the internal volume comprising: a first portion configured to accommodate at least a portion of an infant's lower body; and a second portion located in a superior position relative to the first portion and configured to accommodate at least a portion of the infant's upper body.

In an embodiment, the sleep garment may further comprise a first accommodation mechanism connected to the body for receiving a support element, the first accommodation mechanism being located proximate to and inferior relative to the first portion at the second side, and wherein the support element, upon being received at the first accommodation mechanism, is configured to support the infant's legs at an elevated angle relative to the infant's hips.

FIG. 1 illustrates an infant sleep garment 100 according to various embodiments described herein. The sleep garment 100 may include a body 102, which may also be referred to herein as a sleep sack, may be configured as a clothing article or an over garment to be worn by an infant. The body 102 may include an infant enclosure region comprising an interior volume. The body 102 may include a coupling mechanism to enclose the infant within the interior volume. The body 102 may be configured to swaddle an infant when within the interior volume thereof. In some embodiments, the body 102 may comprise a sleep sack as described in U.S. patent application Ser. No. 15/055,077, filed Feb. 26, 2016, titled Infant Calming/Sleep-Aid and SIDS Prevention Device with Drive System, or U.S. patent application Ser. No. 15/336,519, filed Oct. 27, 2016, titled Infant Calm/Sleep-Aid, SIDS Prevention Device, and Method of Use. The disclosures of both of which are hereby incorporated herein by reference.

With reference to FIGS. 1-5, body 102 has first side 104 and second side 106 opposite first side 104, first side 104 and second side 106 defining internal volume 108 therebetween. Internal volume 108 comprises first portion 110 configured to accommodate at least a portion of an infant's lower body. In an embodiment, a width of first portion 110 may be the average width of an infant's hips, or a circumference of first portion 110 may be the average waist circumference of an infant. In an embodiment, first portion 110 may be a material with elastic properties that shrinks or expands to accommodate at least a portion of an infant's lower body, or may be adjustable such that a user may set an appropriate dimension of first portion 110 to accommodate an infant's lower body.

Internal volume 108 may further define a second portion 112 located in a superior position relative to the first portion 110 and configured to accommodate the infant's upper body. The internal volume 108 may further define a third portion 113 located in an inferior position relative to the first portion 110 and configured to accommodate the infant's feet. In the context of the present disclosure, a superior position is one relatively further towards the head of an infant, while an inferior position is one relatively further towards the feet of an infant.

Figure 2:
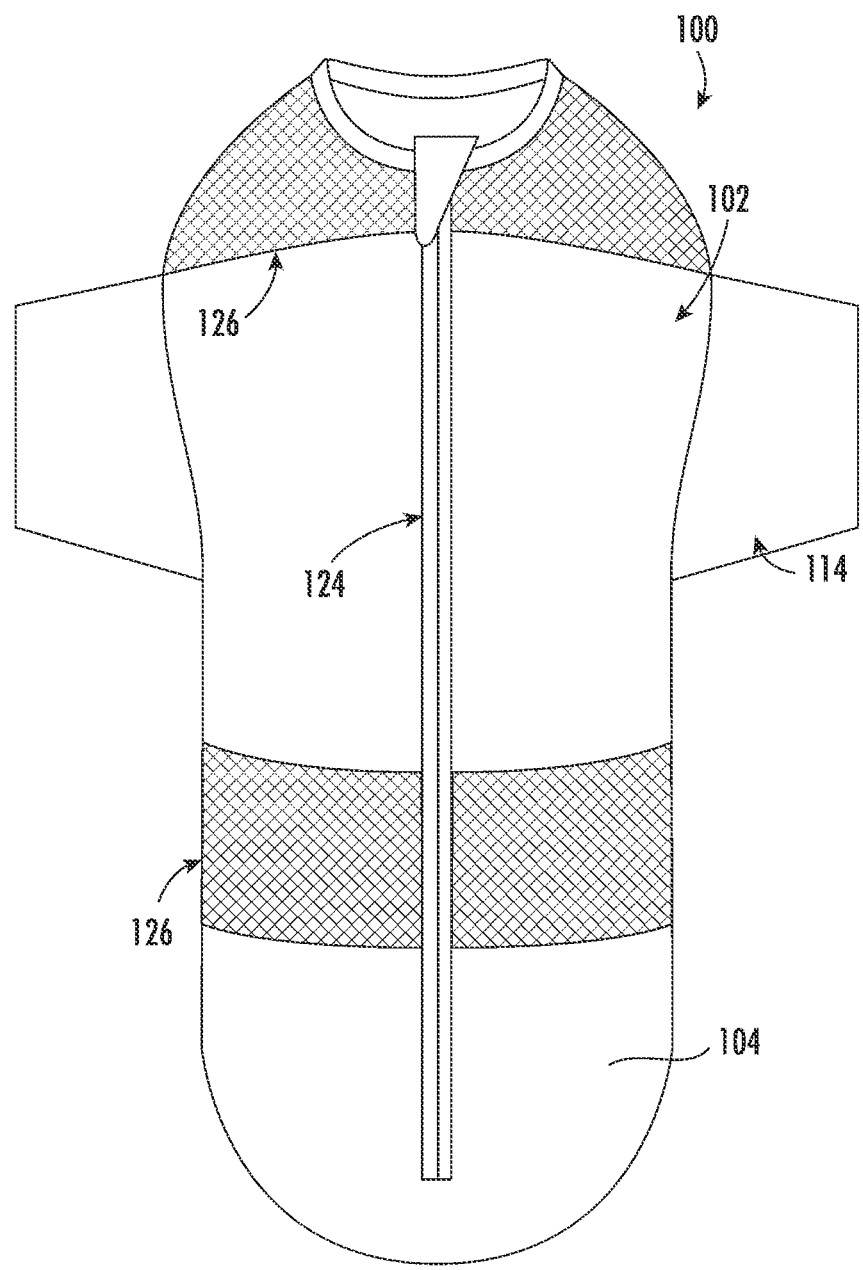
FIG. 2 is a top-down perspective view illustration of the first side of an infant sleep garment according to various embodiments described herein.

FIG. 2 is a top-down perspective view illustration of the first side 104 of infant sleep garment 100. In the example shown in FIG. 2, the first side 104 may comprise a first coupling mechanism 124 coincident with the sagittal plane of the infant and allowing access to the internal volume 108. A portion of the body 102 may comprise a mesh fabric 126 for allowing air to move therethrough. First coupling mechanism 124 may include but is not limited to any sealable and un-sealable mechanism, such as a zipper mechanism, a hook and loop attachment mechanism, a push snap attachment, a magnetic attachment mechanism, fasteners, clips, buttons, or any similar mechanism.

Figure 7:
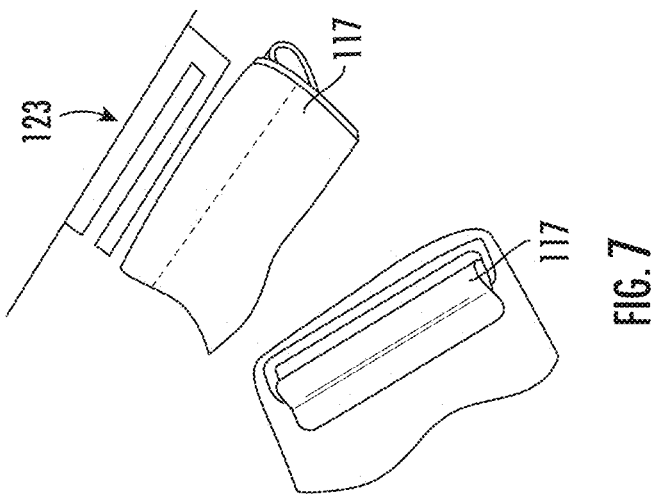
FIG. 7 is a perspective view illustration of a first securing mechanism according to various embodiments described herein.
Figure 6:
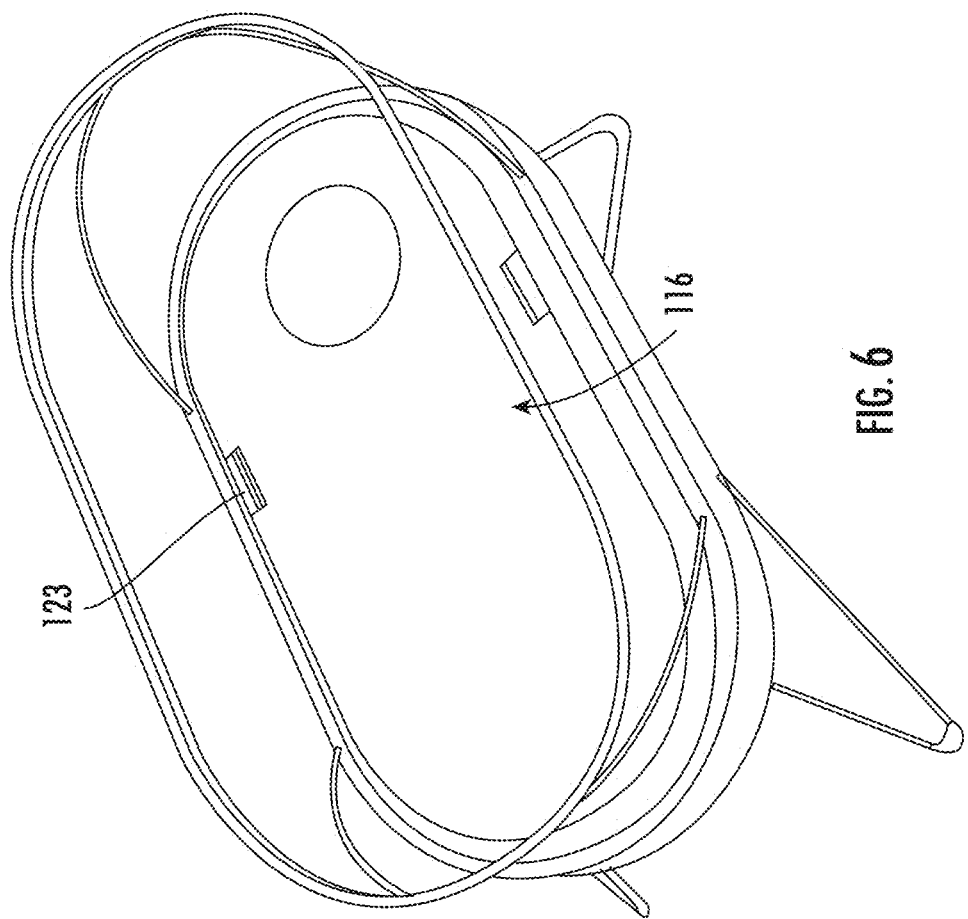
FIG. 6 is perspective view illustration of a sleep surface according to various embodiments described herein.

FIG. 2 also shows an embodiment of a first securing mechanism 114. First securing mechanism 114 is connected to the body 102 and configured to fix the sleep garment to a sleep surface 116 (shown in FIG. 6). In the illustrated embodiment, the first securing mechanism 114 includes first and second material expanses 114a, 114b that extend outwardly of the body 120. In an embodiment, the first securing mechanism 114 may be any mechanism configured to secure the sleep garment 100 to sleep surface 116 to prevent an infant inside a sleep garment from rolling over or otherwise moving into an unsafe disposition. The first securing mechanism 114 may include but is not limited to any of the following: a strap configured to attach to a clip, an elastic strap, a hook and loop attachment mechanism, a push snap attachment, a zipper mechanism, a magnetic attachment mechanism, or any similar mechanism configured to secure sleep garment 100 to sleep surface 116. An embodiment of a securing mechanism 114 may comprise a sleeve 117 or clip 123 positioned on the first or second expanse of material 114a, 114b, for engaging a corresponding clip or sleeve, which may be connected to the sleep surface 116, e.g., in a manner shown in FIG. 7. In an embodiment, the first securing mechanism 114 of the sleep garment 100 may be configured to attach to another garment, or sleep garment 100 may be accommodated within another garment, wherein the other garment is attachable to sleep surface 116, thereby indirectly securing the sleep garment 100 to sleep surface 116.

Figure 3:
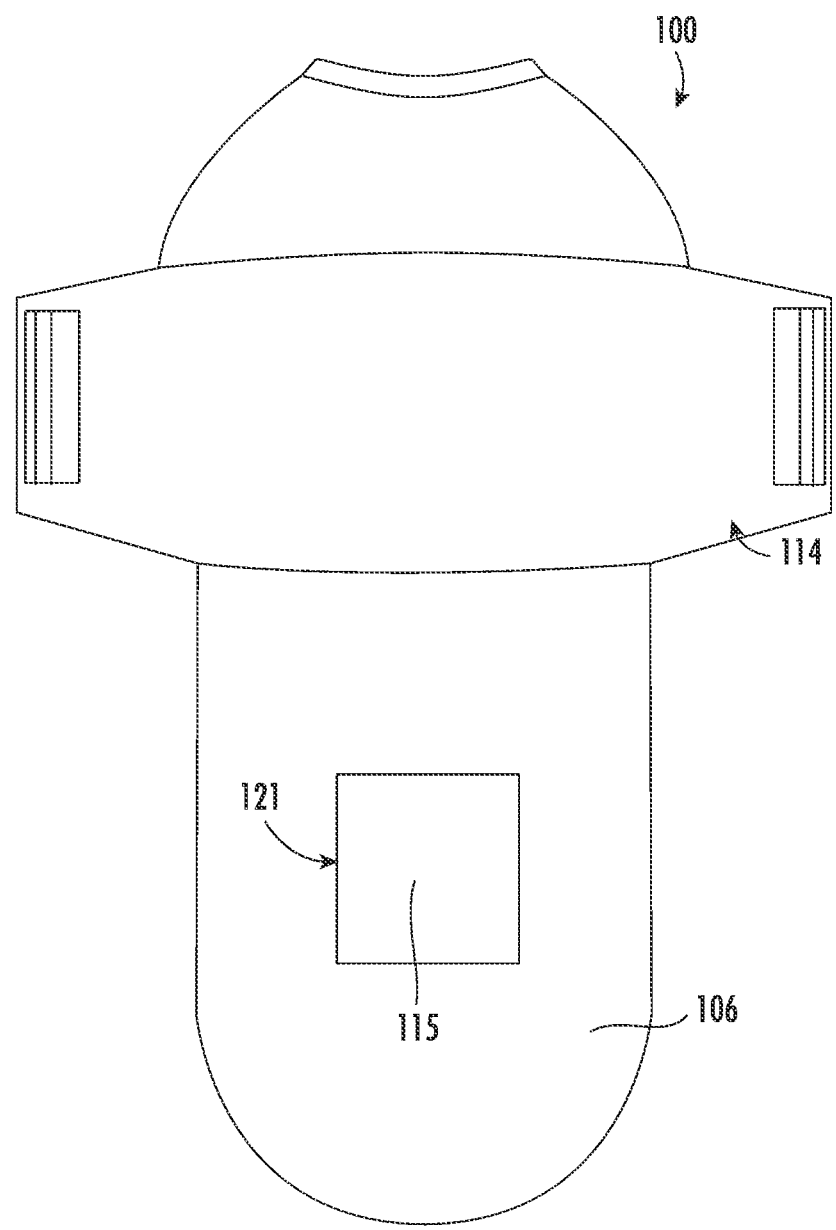
FIG. 3 is a bottom-up perspective view illustration of the second side of an infant sleep garment according to various embodiments described herein.
Figure 8:
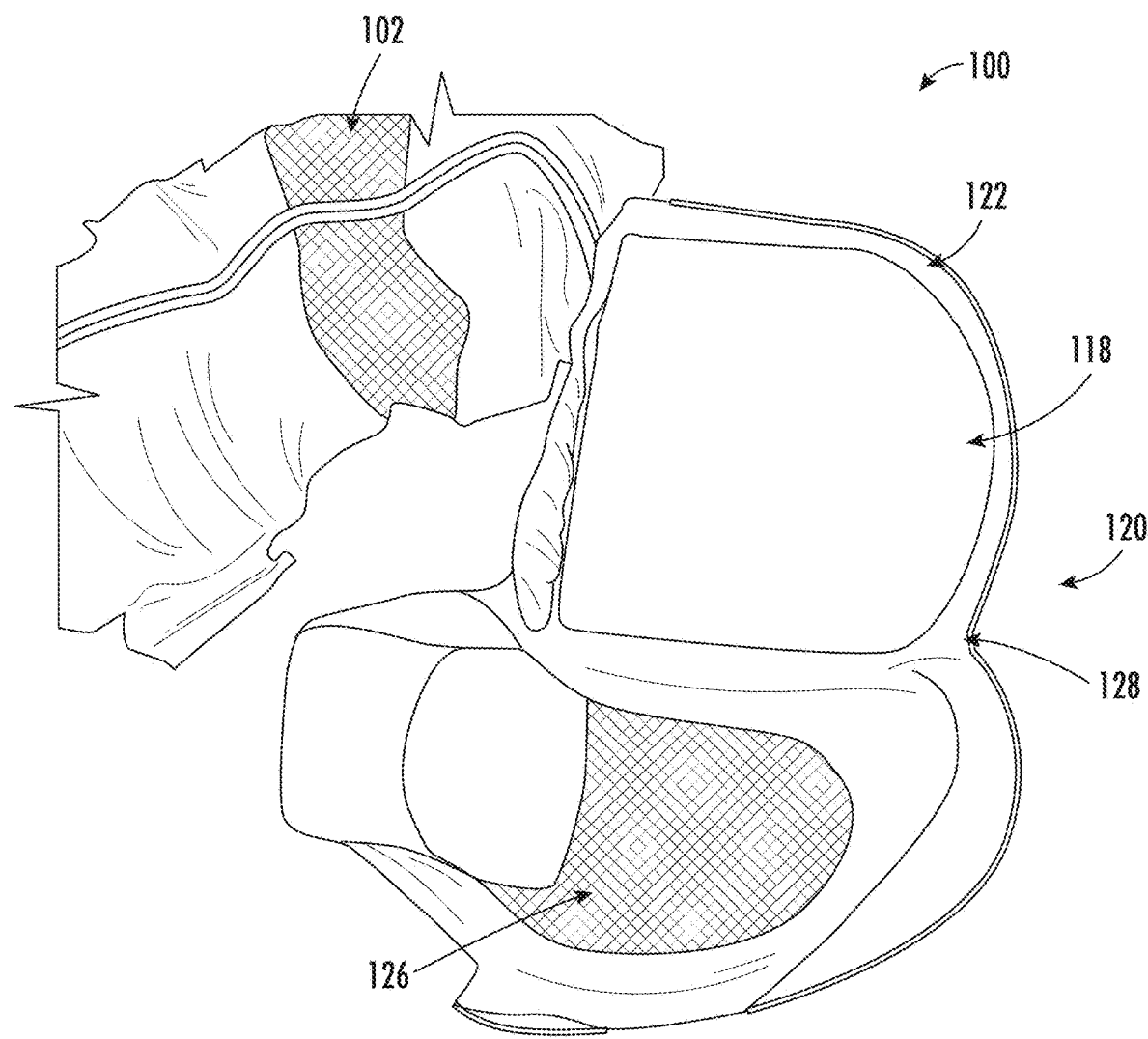
FIG. 8 is a perspective view of an outer enclosure according to various embodiments described herein.
Figure 9:
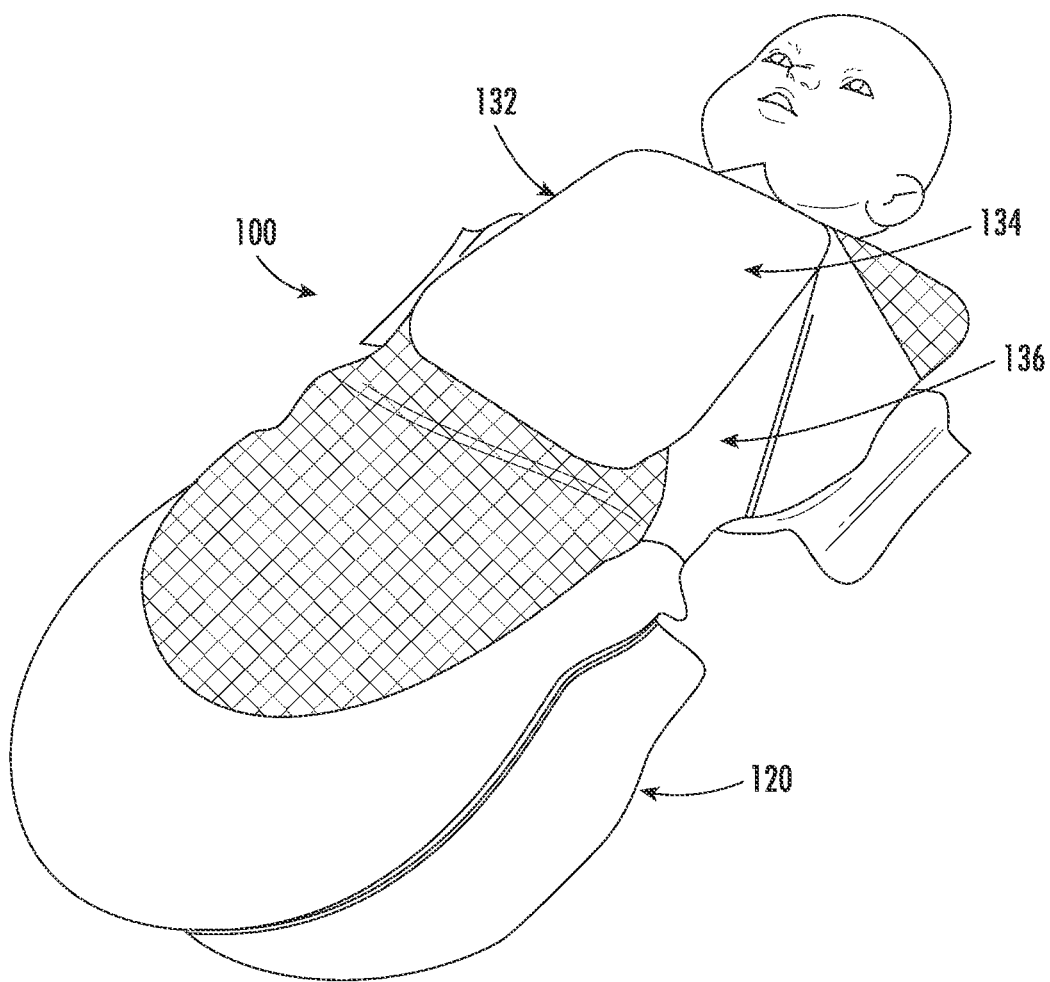
FIG. 9 is a perspective view of an outer enclosure according to various embodiments described herein.

With particular reference to FIGS. 1-3, a support element 118 may be configured to be received at location 115 that is proximate to and inferior relative to the first portion 110 at the second side 106, thereby supporting the infant's legs at an elevated angle relative to the infant's hips. In an embodiment, support element 118 may be placed at location 115 by a user, without an attachment mechanism. In the embodiment shown in FIGS. 1-3, support element 118 may be received at first accommodation mechanism 121 located at location 115 that is proximate to and inferior relative to the first portion 110 at the second side 106. The first accommodation mechanism 121 may be connected to the body 102 of sleep garment 100 as shown in FIG. 3, or may be connected to the sleep surface 116 of FIG. 6, or may be connected to outer enclosure 120 which may receive support element 118, as shown in FIGS. 8-9. The first accommodation mechanism 121 may include but is not limited to any mechanism configured to receive support element 118, such as a pocket, an enclosure, a strap configured to attach to a clip, an elastic strap, a hook and loop attachment mechanism, a push snap attachment, a zipper mechanism, a magnetic attachment mechanism, or any similar mechanism configured to receive support element 118.

It is to be appreciated that the support element 118 may be configured to have different shapes and dimensions in accordance to the principles disclosed there. In an embodiment, a surface 119 of the support element 118 may be flat, inclined upwardly or downwardly, rounded, recessed, partially inclined or any combination thereof. In an embodiment, the surface 119 may be inclined from one end to another end, as shown in FIG. 1. In an embodiment, a support element may comprise a flat surface. In an embodiment shown in FIG. 13, support element 212 may comprise a first portion 230 and a second portion 232, first portion 230 comprising a flat surface and second portion 232 comprising an inclined surface. The incline of the surfaces 119 and 232 may be configured to promote a desired elevated angle between the infant's legs and hips. In an embodiment, the elevated angle relative to the infant's hips may be between 30 and 160 degrees, which is a range that may be effect in comforting certain infants. The raising of an infant's legs to within this range may preferably relax the infant's abdomen muscles, promoting a calming reflex. In an embodiment of a support element, there may be multiple upwardly or downwardly inclined, flat, or otherwise shaped portions from a proximal to a distal end. A support element may comprise other shapes and geometries in accordance to the principles disclosed herein. For example, in an embodiment, a surface of the support element may be contoured to accommodate each leg of an infant separately. In an embodiment, the height of a distal end of the support element may be lower than that of the proximal end.

In an embodiment, the support element 118, upon being received at the location 115 that is proximate to and inferior relative to the first portion 110 at the second side 106, may be located outside the interior volume 108.

In an embodiment, the support element 118 may be received at first accommodation mechanism 121 located at location 115 outside the interior volume 108 by connecting the support element 118 to the sleep surface 116. It is to be appreciated that the support element 118 may be connected to the sleep surface 116 by any type of connectors (not shown) in accordance with the principles of the present disclosure. For example, the support element 118 may be connected to sleep surface 116 by a strap configured to attach to a clip, an elastic strap, a hook and loop attachment mechanism, a push snap attachment, a zipper mechanism, a magnetic attachment mechanism, or any similar mechanism configured to connect support element 118 to sleep surface 116. In an embodiment, support element 118 may also be inserted into an accommodation space (not shown) of sleep surface 116.

In an embodiment, the support element 118 may be received at the location 115 that is proximate to and inferior relative to the first portion 110 at the second side 106 by connecting the support element 118 to the body 102 of the garment 100. Support element 118 may be connected to body 102 at the second side 106 by any type of connectors (not shown) in accordance with the principles of the present disclosure. For example, the support element 118 may be connected to the garment 100 by a strap configured to attach to a clip, an elastic strap, a hook and loop attachment mechanism, a push snap attachment, a zipper mechanism, a magnetic attachment mechanism, or any similar mechanism configured to attach support element 118 to second side 106. In an embodiment, support element 118 may also be inserted into an accommodation space (not shown) defined on the exterior or interior of the second side 106 of the garment 100.

In an embodiment, the support element 118, upon being received at the location 115 that is proximate to and inferior relative to the first portion 110 at the second side 106, may be located inside the interior volume 108. For example, an accommodation space (not shown) may be defined by a compartment between the first and second sides 104, 106 of the garment 100 for receiving the support element 118 in the interior volume 108.

In an embodiment, the support element 118, upon being connected to the garment 100, may be located outside the interior volume 108. For example, the garment 100 may further include an outer enclosure 120 for enclosing the support element 118 in a compartment 122 outside the body 102.

FIG. 8 is a perspective view of an embodiment of the outer enclosure 120. The outer enclosure 120 may be configured to accommodate a portion of the body 102 therein and define an internal compartment 122 for accommodating the support element 118 and the third portion 113 of the body 102. The support element 118, upon being accommodated in the internal compartment 122, may be received at the location 115 that is proximate to and inferior relative to the first portion 110 at the second side 106 and under the third portion 113.

In FIG. 8, the outer enclosure 120 may comprise a second coupling mechanism 128 extending at least partially around the periphery of outer enclosure 120. In an embodiment, the second coupling mechanism 128 may be a strap configured to attach to a clip, an elastic strap, a hook and loop attachment mechanism, a push snap attachment, a zipper mechanism, a magnetic attachment mechanism, or any similar mechanism configured to seal and unseal outer enclosure 120 to accommodate body 102 therein. At least a portion of the outer enclosure 120 may comprise mesh fabric 126 for allowing air to move therethrough. In an embodiment, at least a surface of the outer enclosure 120 proximate to the second surface may be comprised entirely of a mesh structure. In an embodiment, a majority of the outer enclosure 120 may comprise a mesh structure.

Referring back to FIG. 1, the infant sleep garment 100 may further comprise a second securing mechanism 130; and the second securing mechanism 130 may be attached to the body 102 and configured to fix an infant within the interior volume 108. The second securing mechanism 130 may include but is not limited to any of the following: a strap configured to attach to a clip, an elastic strap, a hook and loop attachment mechanism, a push snap attachment, a zipper mechanism, a magnetic attachment mechanism, or any similar mechanism configured to fix an infant within the interior volume 108. The second securing mechanism 130 may be located inside the interior volume 108 or may be located outside the interior volume 108, and may be proximate the first portion 110, second portion 112, or third portion 113.

In FIG. 9, the sleep garment 100 may be configured to receive a weight element 132 at a location 134 proximate to the second portion 112 at the first side 104 of the body 102, thereby applying pressure to the infant's body. In an embodiment, a sleep garment may be configured to receive a weight element at a location to thereby apply pressure to the infant's upper body, lower body, or both upper and lower body simultaneously.

In an embodiment, the second portion 112 of the internal volume 108 may comprise a compartment (not shown) to receive the weight element 132 at the location 134 proximate to the second portion 112 at the first side 104 of the body 102.

In an embodiment, the weight element 132 may be received at the location 134 proximate to the second portion 112 at the first side 104 of the body 102 by connecting the weight element 132 to the first side 104 of the body 102 by a connector (not shown) which may include but is not limited to any of the following: a strap configured to attach to a clip, an elastic strap, a hook and loop attachment mechanism, a push snap attachment, a zipper mechanism, a magnetic attachment mechanism, or any similar mechanism.

In FIG. 9 the outer enclosure 120 further may comprise a second compartment 136 for accommodating the weight element 132 at the location 134 proximate to the second portion 112 at the first side 104 of the body 102.

In an embodiment, the weight element 132 may weigh between 1 ounce and 3 pounds, preferably between 0.5 and 1.5 pounds, between 1 and 1.5 pounds, or about 5 pounds, about 0.75 pounds, about 1 pound, about 1.25 pounds, or about 1.5 pounds, or about 1.75 pounds. By positioning the weight element 132 at location 134 proximate an infant's chest, the pressure applied by the weight element 132 may elicit a calming response from the infant, aiding in the sleep of the infant. Further, upon being received at location 134, the weight element 132 may be fixed relative to an infant within the sleep garment, and may be prevented from interfering with the sleep of the infant. In an embodiment, the pressure applied by weight element 132 upon being received at location 134 may be distributed over the chest and stomach of the infant. In an embodiment, the pressure from the weight element may be at least partially distributed over the lower body of the infant as well. In an embodiment, the weight element may be received at an alternate location (not shown) to thereby distribute a portion of the weight over the upper body and a portion of the weight over the lower body.

In an embodiment, the weight element 132 may be received at the location 134 proximate to the second portion 112 at the first side 104 of the body 102 by connecting the weight element 132 to the second portion 112 by a connector (not shown) which may include but is not limited to any of the following: a strap configured to attach to a clip, an elastic strap, a hook and loop attachment mechanism, a push snap attachment, a zipper mechanism, a magnetic attachment mechanism, or any similar mechanism.

In an embodiment, the weight element 132 may comprise any weighted material which may include but is not limited to a metal, a plastic, a ceramic, a polymer, gel, liquid, a composite, a natural, or an artificial material. Furthermore, the weight may be flat, round, irregular or any other shape and further may be any size so as to be effective for its functions described herein.

Figure 10:
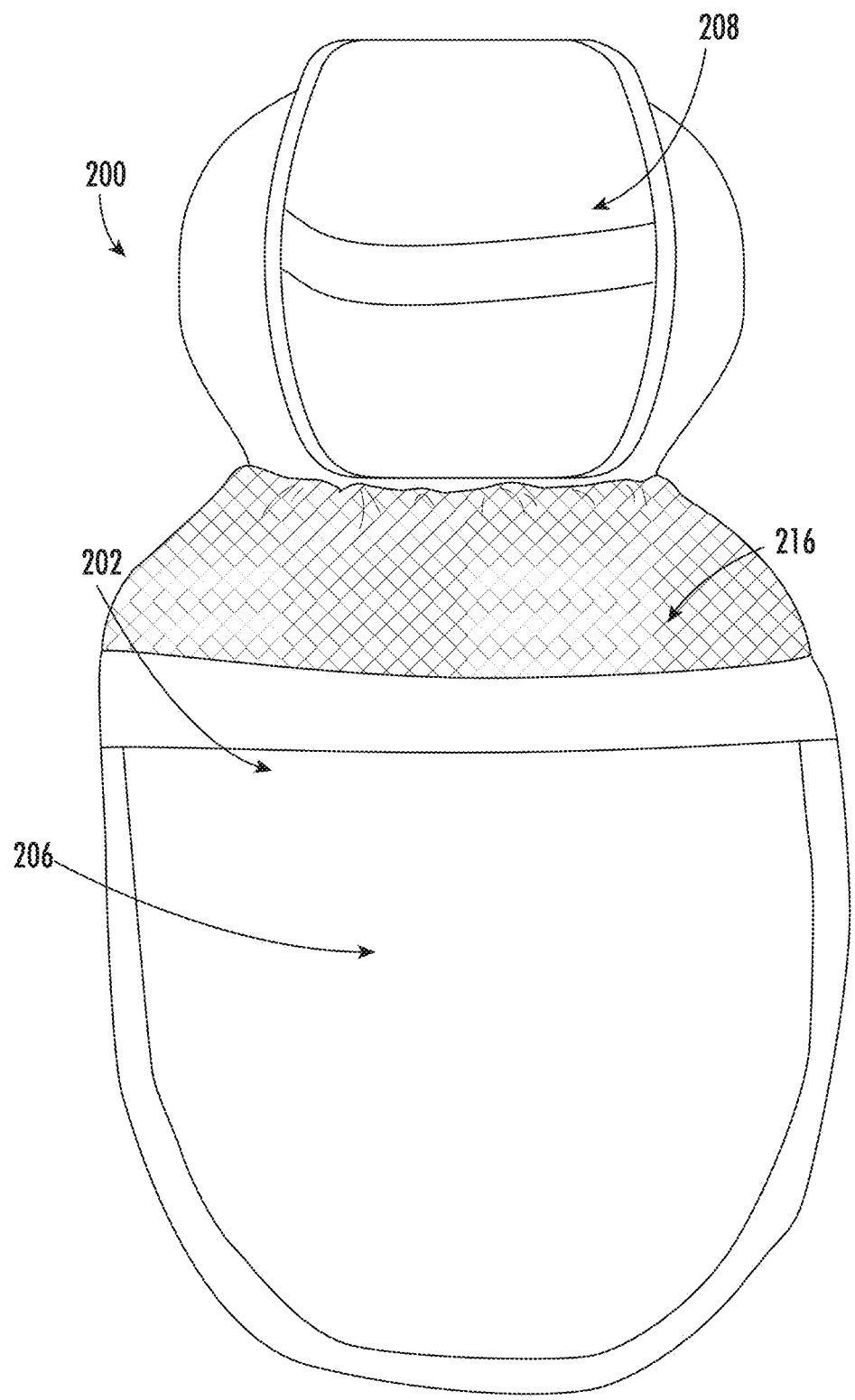
FIG. 10 is a bottom view of an enclosure for accommodating an infant according to various embodiments described herein.
Figure 11:
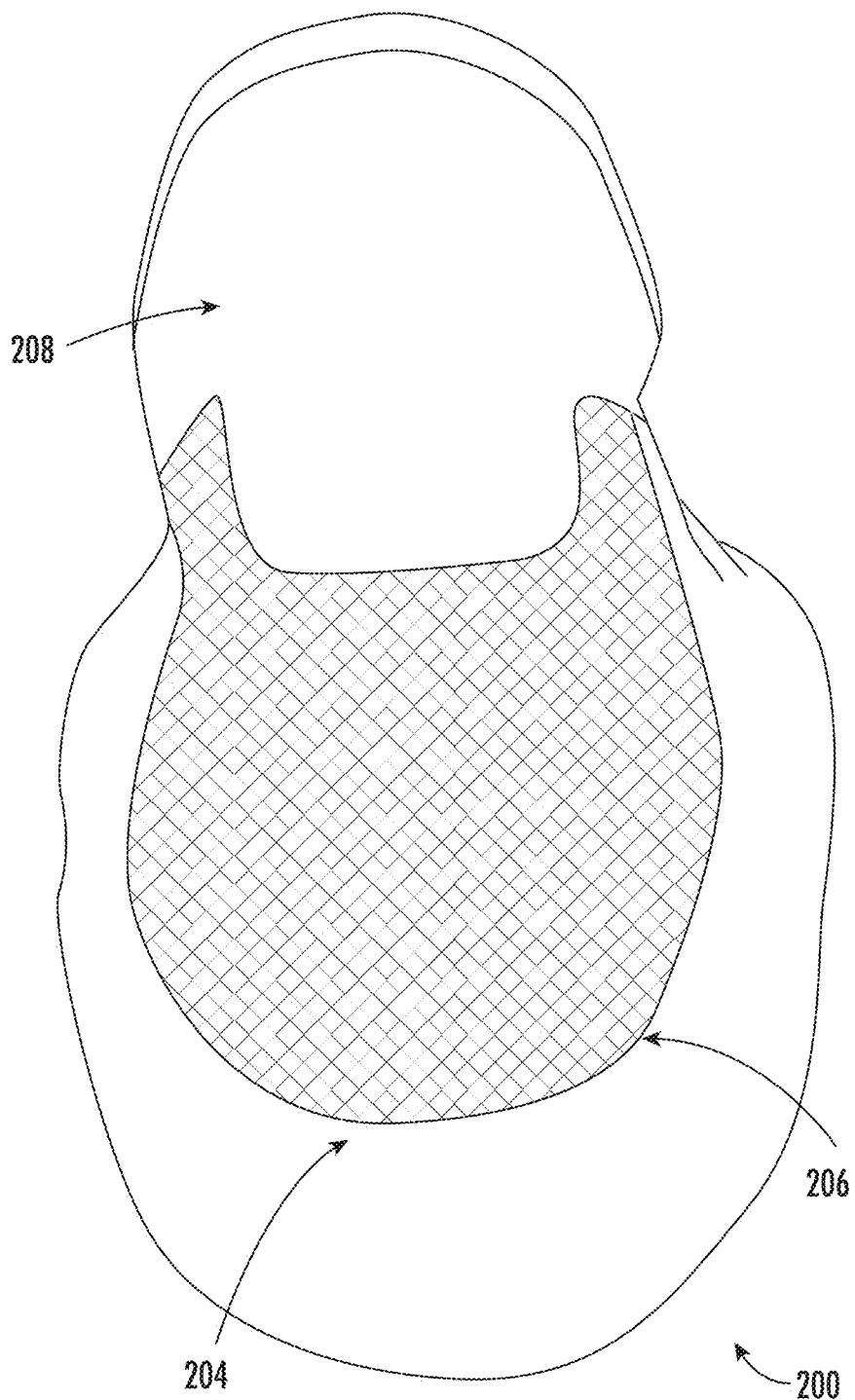
FIG. 11 is a top view of an enclosure for accommodating an infant according to various embodiments described herein.
Figure 12:
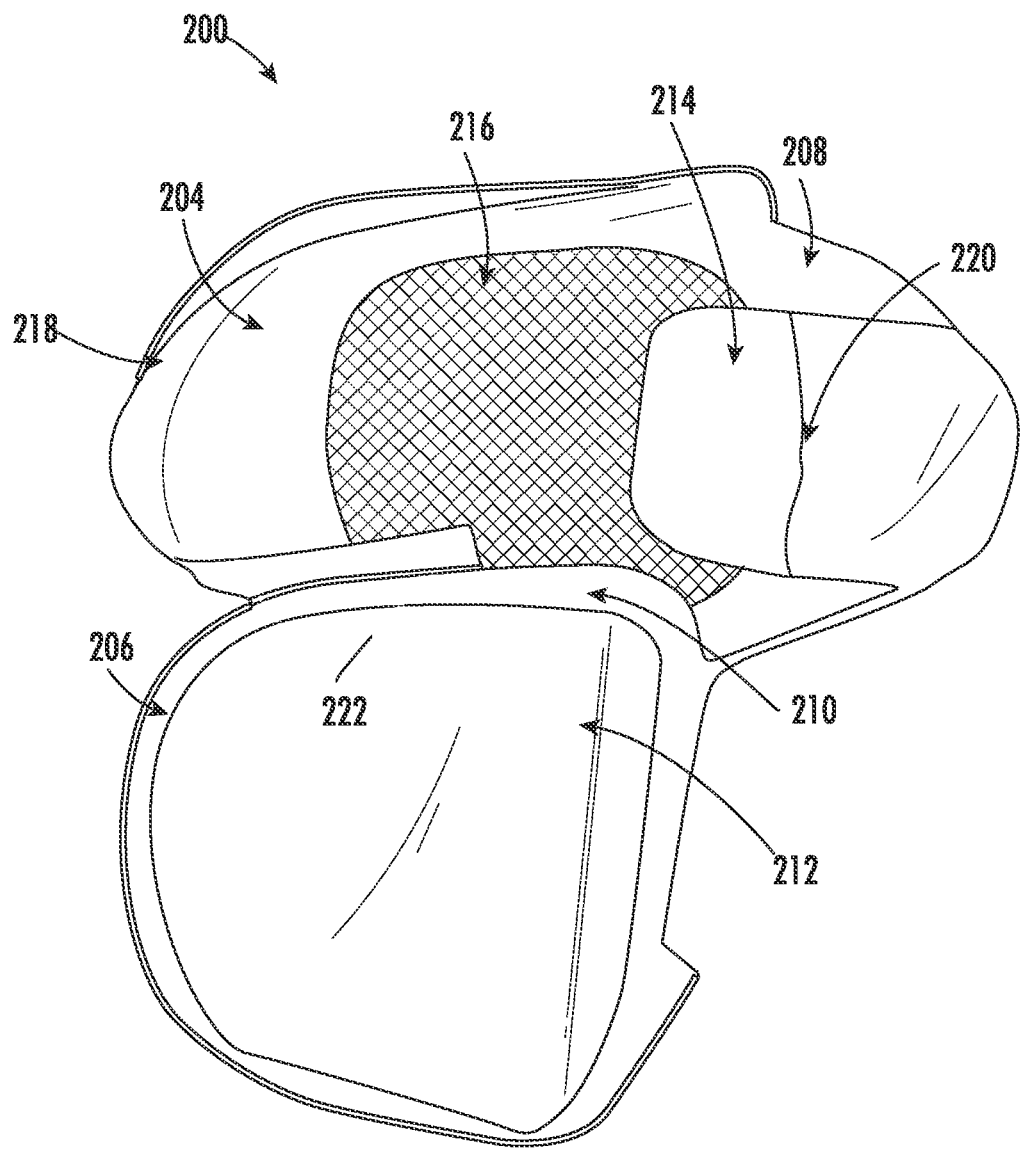
FIG. 12 is a top view of an opened enclosure for accommodating an infant according to various embodiments described herein.

FIGS. 10-12 illustrate an embodiment of an enclosure 200 for accommodating an infant. FIG. 11 shows a view of first side 204, while FIG. 10 shows a view of second side 202, which is opposite first side 204.

Enclosure 200 comprises a first portion 206 configured to accommodate an infant's legs between the first side 204 and the second side 202. Enclosure 200 may further comprise a second portion 208 configured to accommodate the infant's torso beneath the first side 204.

The second side 202 is configured to couple with a support element 212. In FIG. 12, first portion 206 comprises a first accommodation mechanism 210 for receiving a support element 212 configured to support the infant's legs at an elevated angle relative to the infant's hips. Furthermore, second portion 208 comprises a second accommodation mechanism 214 for receiving a weight element (not shown) for applying pressure to an infant's torso.

Referring to FIGS. 10-12, portions of first side 204 and second side 202 comprise a mesh fabric 216 for allowing air to move therethrough. First side 204 and second side 202 are partially connected by coupling mechanism 218, which extends partially around the periphery of first portion 206.

In FIG. 12, the first accommodation mechanism 210 comprises a compartment 222 for receiving the support element 212 therein, and second accommodation mechanism 214 comprises compartment 220 for receiving the weight element (not shown) therein. Furthermore, first side 204 and second side 202 are configured to at least partially accommodate an infant sleep garment, such as sleep garment 100, therebetween. In an embodiment, enclosure 200 may be configured to attach to a sleep surface, such as sleep surface 116. In an embodiment, upon enclosure 200 accommodating a sleep garment such as sleep garment 100 therewithin, the sleep garment may be configured to attach to a sleep surface such as sleep surface 116, thereby fixing enclosure 200 to the sleep surface. In an embodiment, the enclosure 200 may alternately be configured to attach to another sleep garment through an attachment mechanism, and the other sleep garment may then be secured to a sleep surface, thereby indirectly securing enclosure 200 to the sleep surface. By attaching the enclosure 200 to a sleep surface, an infant accommodated within enclosure 200 may be prevented from rolling over or otherwise moving into an unsafe disposition.

In an embodiment, the enclosure 200 may comprise a first securing mechanism for securing an infant within the enclosure according to the principles disclosed herein. In an embodiment, the enclosure 200 may comprise a second securing mechanism for securing the enclosure 200 to a sleep surface, such as sleep surface 116, according to the principles disclosed herein. The second securing mechanism may prevent an infant accommodated with the enclosure 200 from rolling over or otherwise moving into an unsafe disposition. Furthermore, the attachment mechanisms disclosed herein may be configured to communicate with a control system to detect whether an attachment mechanism is properly secured, and may alert a user or cease some operational function upon detecting that an attachment mechanism is not properly secured.

Referring to FIGS. 10-12, an infant may be placed proximate to enclosure 200, with the infant's hips adjacent to support element 212 and legs positioned on a top surface of support element 212. A user may then operate coupling mechanism 218, partially sealing first side 204 on top of second side 202, accommodating the infant and support element 212 within compartment 222. First side 204 will then be located above the infant, with compartment 220 positioned proximate to the infant's torso.

Figure 13:
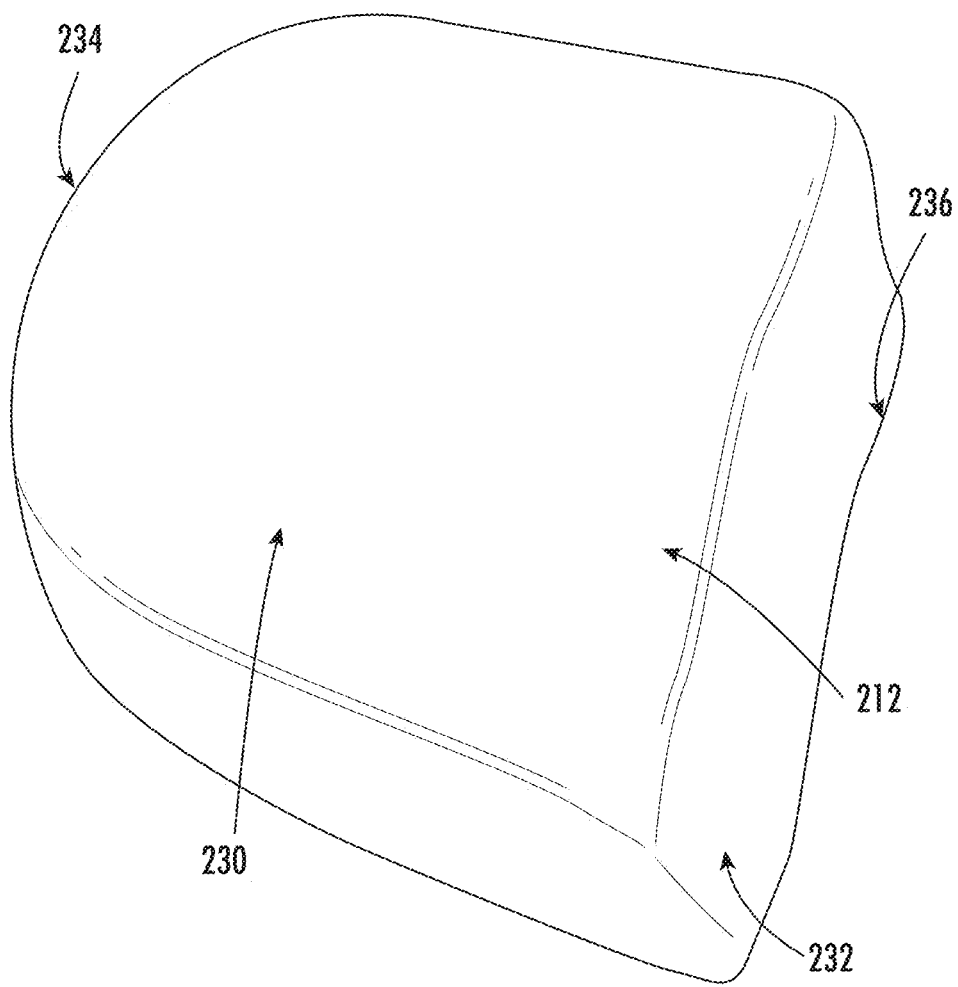
FIG. 13 is a perspective view of a support element according to various embodiments described herein.

FIG. 13 illustrates an embodiment of support element 212. Support element 212 comprises a first portion 230 and a second portion 232. First portion 230 is flat, while second portion 232 is inclined from a proximal end 236 to a distal end 234. Support element 212 at the first portion 230 is a constant thickness, and has a rounded, bullnose shape at the distal end 234 and a straight edge at the proximal end 236. In embodiments, a support element may include but is not limited to a foam material, a cushion, an air pocket, or any material configured to support an infant's legs in an elevated angle relative to the infant's torso. The support element may further comprise a fabric case (not shown) surrounding the supportive material. The support element may have a resistance to deformation configured to support the infant's legs in the elevated position according to the principles disclosed herein. The support element and/or the fabric case may also be resistant to liquid or biological materials.

In an embodiment, sleep garment 100 may be configured to accommodate a pillow, gel pad or other type of support (not shown) beneath the head of an infant. In an embodiment, enclosure 200 may be configured to accommodate a pillow, gel pad or other type of support (not shown) beneath the head of an infant.

FIGS. 14-17B illustrate an enclosure 300 according to various embodiments. The enclosure 300 may be configured to accommodate an infant, which, in some embodiments, may include all or a portion of a body 102 (see, e.g., FIG. 1) further enclosing or swaddling the infant therein.

Figure 15:
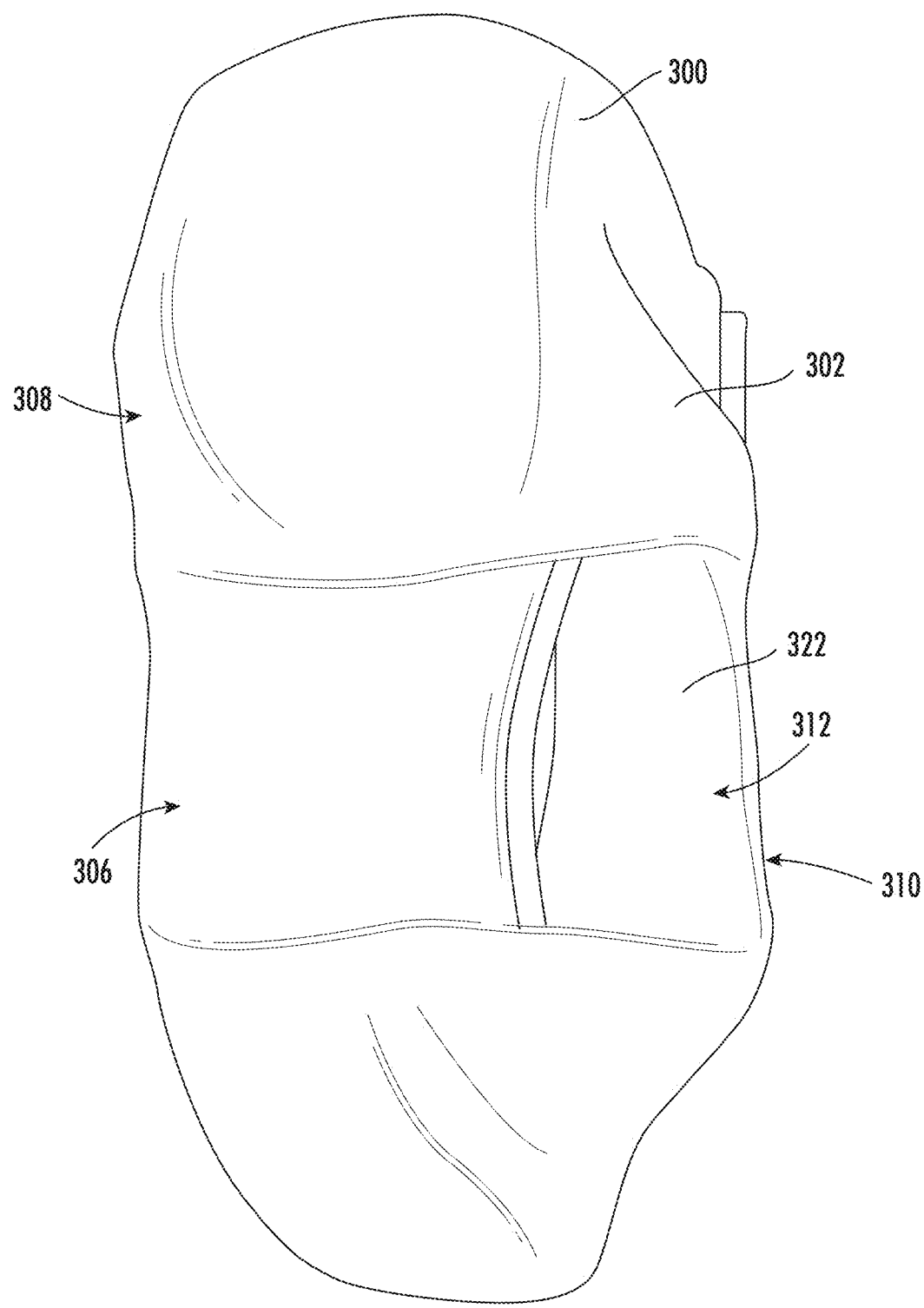
FIG. 15 is a bottom view of an enclosure including a second side according to various embodiments described herein.
Figure 16:
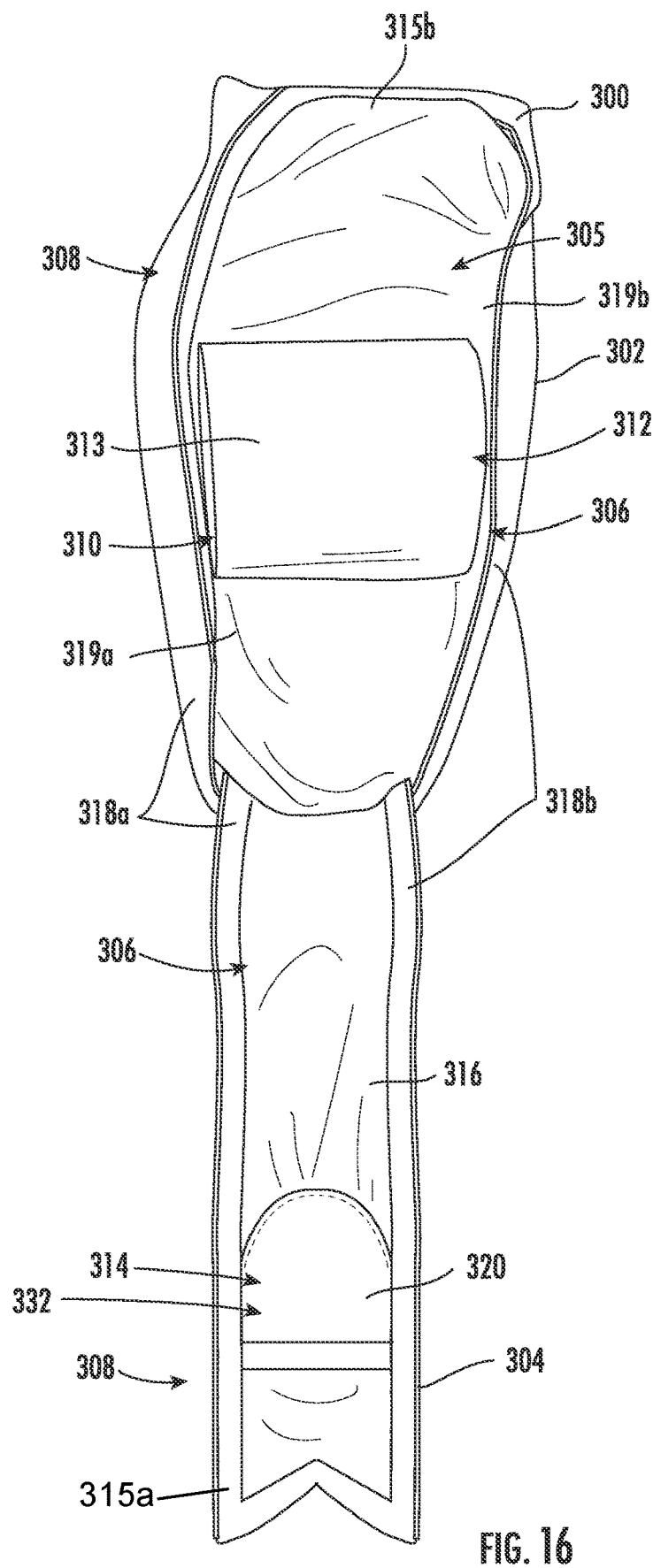
FIG. 16 is a top view of an enclosure wherein a first side has been folded down to review an enclosure volume according to various embodiments described herein.

The enclosure 300 includes a first side 304 (FIG. 14) and a second side 302 (FIG. 15) that together define an enclosure volume 305 (FIG. 16) between their respective interior surfaces. FIG. 16 illustrates the first side 304 partially separated or detached from the second side 302. The first and second sides 304, 302 may remain attached along a portion of their respective perimeters as shown or along another perimeter portion or may be completely separated (not shown). The enclosure 300 further comprises a first portion 306 configured to accommodate the lower body of an infant within the enclosure volume 305 between the first side 304 and the second side 302. The enclosure 300 may further comprise a second portion 308 configured to accommodate a torso of an infant within the enclosure volume 305 between the first side 304 and the second side 302.

The enclosure 300 may include one or more areas comprising mesh fabric 316 to provide breathability and reduce overheating. For example, the first side 304, the second side 302, or both may include one or more areas comprising a mesh fabric 316. In the illustrated embodiment, the first side 304 includes an area comprising a mesh fabric 316 along the first portion 306 defining a region of the enclosure volume 305 corresponding to a region for enclosing the legs of an infant. The second side 302 includes one or more areas of fabric mesh 316 along the second portion 308 defining a region of the enclosure volume 305 corresponding to regions for enclosing arms or shoulders of an infant. In an embodiment, at least a surface of the enclosure 300 proximate to the first portion 306 may be comprised entirely of a breathable mesh structure. In a further embodiment, a majority of the enclosure 300 may comprise a breathable mesh structure.

The enclosure 300 may be configured to include or associated with one or more accommodation mechanisms. The accommodation mechanisms may be similar to the accommodation mechanisms described above with respect to FIGS. 1-13 and elsewhere herein. In the illustrated embodiment, the first side 304 is configured to couple with a weight element 332 and the second side 203 is configured to couple with a support element 312. For example, the enclosure 300 is configured to include or associate with an accommodation mechanism 314 comprising a weight element 332 and an accommodation mechanism 310 comprising a support element 312. As shown, the enclosure 300 is configured to receive a weight element 332 at a location 335 proximate to the second portion 308 at the first side 304. The weight element 332 may be positioned such that it applies weight to the upper body, chest, and/or abdominal area of an infant enclosed in the enclosure 300. In the illustrated embodiment, as best shown in FIG. 16, a compartment 320 comprising a pocket is positioned on the first side 304 for receiving the weight element 332. The compartment 320 is accessible from the interior side of the first side 304. In one embodiment, the first side 304 includes a compartment 320 accessible from its exterior side or that is sewn, adhered, or otherwise closed, with the weight element 332 enclosed therein. In some embodiments, the first side 304 is configured to removably couple with the weight element via snaps, straps, clips, hook and loop, mating structures, or other coupling structures.

In some embodiment, the weight element 332 may weigh between 1 ounce and 3 pounds, preferably between 0.5 and 1.5 pounds, between 1 and 1.5 pounds, or about 5 pounds, about 0.75 pounds, about 1 pound, about 1.25 pounds, or about 1.5 pounds, or about 1.75 pounds. By positioning the weight element 332 at location 335, which corresponds to an upper body location proximate a chest of an infant, the pressure applied by the weight element 332 may be applied to a chest or abdominal area and elicit a calming response from the infant, aiding in the sleep of the infant. Further, upon being received at location 335, the weight element 332 may be fixed relative to an infant within the enclosure 300, and may be prevented from interfering with the sleep of the infant. In an embodiment, the pressure applied by weight element 332 upon being received at location 335 may be distributed over the chest and stomach of the infant. In an embodiment, the pressure from the weight element 332 may be at least partially distributed over the lower body of the infant as well. In an embodiment, the weight element 332 may be received at an alternate location (not shown) to thereby distribute a portion of its weight over the upper body and a portion of the weight over the lower body of an infant enclosed in the enclosure 300.

In some embodiments, the weight element 332 may comprise any weighted material which may include but is not limited to a metal, a plastic, a ceramic, a polymer, gel, liquid, a composite, a natural, or an artificial material. Furthermore, the weight may be flat, round, irregular or any other shape and further may be any size so as to be effective for its functions described herein.

As introduced above, enclosure 300 also includes a support element 312. The support element 312 may extend within the enclosure volume 305 and include a structure dimensioned to elevate the lower body, legs, and/or feet of an infant, e.g., from between 0 and 8 inches, such as between 3 and 6 inches, between 4 or 4.5 and 5.5 inches, at least or greater than 4 inches, or approximately 5 inches +/−¼ inch. The support element 312 may extend from the interior side of the second side 302 so as to underlay the legs of an infant when enclosed in the enclosure volume 305. The support element 312 may include an upper surface 313 positioned to underlay the lower body, legs, and/or feet of the infant and that extends a distance from the second side 302 corresponding to the elevation distance the support element 312 is configured to elevate the lower body, legs, and/or feet. The elevation and operable perimeter surface for contacting an infant's lower body, legs, and/or feet is preferably sufficient to produce a bend in the hips and elevate the feet of the infant. The support element 312 may be configured to support the infant's legs at an elevated angle relative to the infant's hips. In some instances, the hips may also contact the support element 312 or otherwise be elevated.

The support element 312 may include various dimensions and cross-section shapes. As best shown in FIG. 16, the illustrated support element 312 includes a generally cylindrical shape having an arcuate shaped cross-section extending from the second side 302. In one embodiment, the support element 312 includes a planar exterior facing surface, an arcuate interior facing surface, and comprises a general "D" shaped cross-section. In another embodiment, the support element 312 is arcuate around its entire or a majority of its perimeter. In other embodiments, the support element 312 comprises other dimensions and cross-section shapes. For example, the support element 312 may comprise geometric, non-geometric, or free form cross-section shapes. In some embodiments, the support element 312 includes inclined, declined, curved, planar, or undulating surfaces. In one embodiment, the top surface 313 comprises an edge formed by the convergence of two sides that form a peak along a length of the support element 312. In one configuration, the support element 312 is dimensioned and shaped as described above with respect to support element 212. In some embodiments, a support element may include but is not limited to a foam material, a cushion, an air pocket, or any material configured to support an infant's legs in an elevated angle relative to the infant's torso. In the illustrated embodiment, the support element 312 is configured to support legs at an elevated angle relative to the hips. The support element 312 comprises a generally cylindrical foam insert approximately 5 inches high configured to produce bend in hips and elevate feet of an infant. The support element 312 may further comprise a fabric case (not shown) surrounding the supportive material. The support element 312 may have a resistance to deformation configured to support the infant's legs in the elevated position according to the principles disclosed herein. In various embodiments, the support element 312 may include contours such as indentations to nest the legs. For example, the top surface, distal facing surface, or proximal facing surface of the support element 312 may include a first indentation to nest a first leg and a second indentation to nest a second leg. Thus, the surfaces within and/or adjacent to the indentations may rise above a back of a leg. In some embodiments, the surfaces within and/or adjacent to the indentations may contact sides of a leg or provide vertically extending obstructions to lateral leg movement. The indentations may be of a constant width or may taper to a reduced width within indentation valleys. The indentations may have planar bases or may include rounded or arcuate laterally extending base surfaces. The support element 312 and/or the fabric case may also be resistant to liquid or biological materials. It will be appreciated that height of the support element 312 or vertical distance the support element 312 extends as described herein is intended to be in reference to the top surface upon which the back or legs or feet are supported.

The support element 312 may be integral or couplable with respect to the second side 302. For example, the enclosure 300 may be configured to receive the support element 312 at a location proximate to the first portion 306 along the second side 302. The support element 312 may be positioned along the first portion 306 such that it elevates the lower body, legs, and/or feet and produces a bend in the hips of an infant enclosed in the enclosure 300. In the illustrated embodiment, as best shown in FIG. 15, a compartment 322 comprising a pocket is positioned on the second side 302 for receiving the support element 312. Thus, the support element 312 may comprise a material insert. The pocket may comprise an envelope enclosure configuration as shown or another configuration. The compartment 322 is accessible from the exterior side of the second side 302. In one embodiment, the second side 302 includes a compartment 322 accessible from its interior side or a compartment 322 that is sewn, adhered, or otherwise sealed closed with the support element 312 enclosed therein. In some embodiments, the second side 302 is configured to removably couple with the support element 312 via snaps, straps, clips, Velcro® or hook and loop, mating structures, or other coupling structures along the exterior or interior side of the second side 302.

Figure 14:
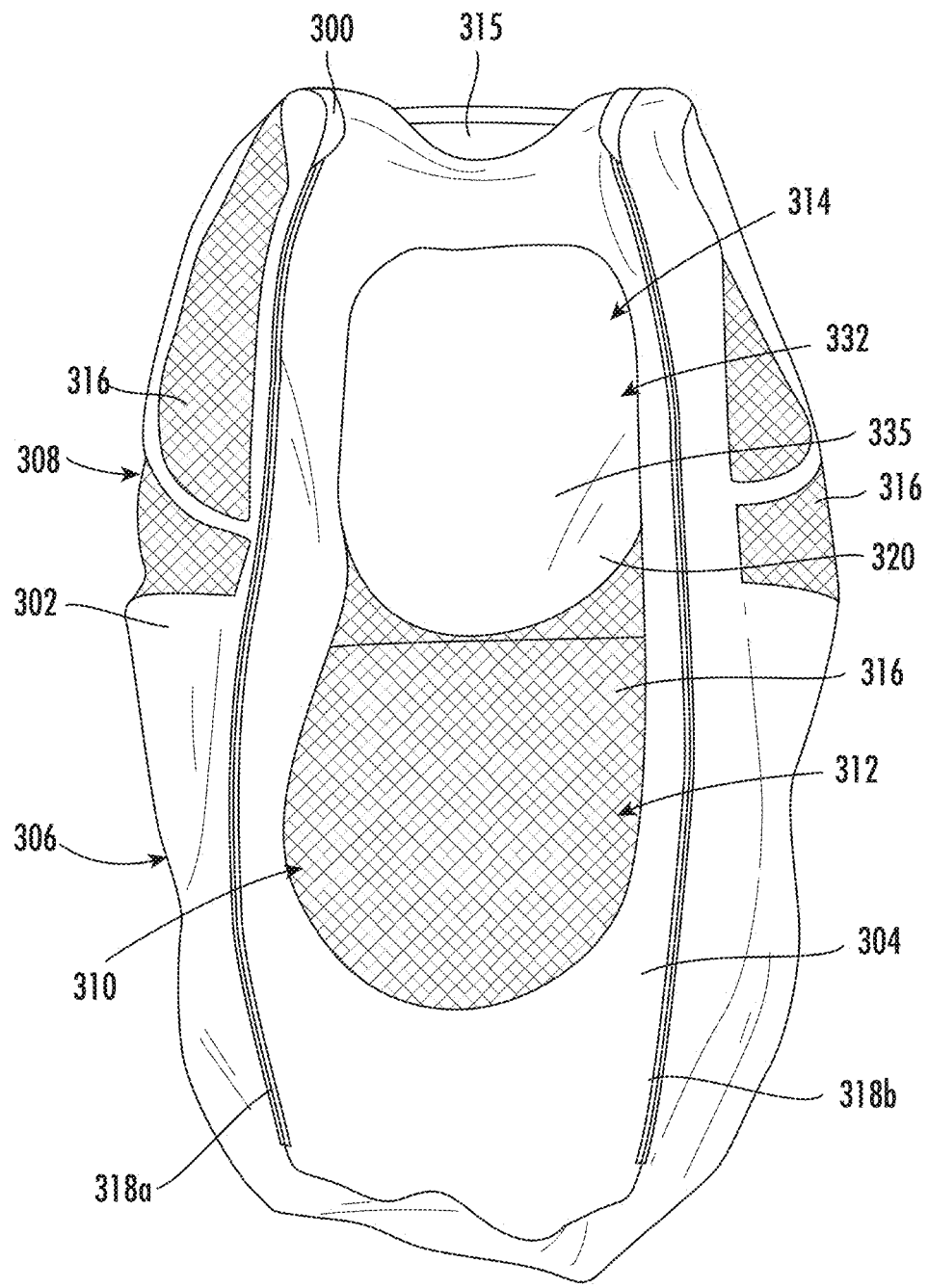
FIG. 14 is a top view of an enclosure including a first side according to various embodiments described herein.

The enclosure 300 may also define one or more selectively openable apertures between the exterior or the enclosure and the enclosure volume 305. In the illustrated embodiment, the enclosure 300 includes a coupling mechanism comprising one or more attachment members 318a, 318b for coupling the first side 304 and the second side 302 and thereby selectively open or close first and second apertures 319a, 319b. The selectively openable apertures are located along lateral peripheries of the first and second sides 304, 302. Attachment members 318a, 318b extend along the adjacent lateral peripheries for coupling the first and second sides 304, 302 to close or reveal the enclosed volume 305. As best shown in FIGS. 14 & 16, the attachment members 318a, 318b comprise zippers wherein adjacent portions of the first and second sides 304, 302 defining the apertures 319a, 319b include zipper halves. In other embodiments, adjacent portions of the first and second sides 304, 302 defining one or more apertures may include snaps, straps, clips, hook and loop, mating structures, or other coupling structures configured to interact to selectively reveal the enclosure volume 305.

In other embodiments, the first side 304 couples to the second side 302 via closure of a single aperture. For example, a selectively openable or closable aperture may extend down a right, left, or middle portion of the first or second sides 304, 302. In a further example, a selectively openable or closable aperture extends diagonally across the first or second sides 304, 302. Some embodiments of the enclosure 300 may include more than two selectively openable or closable apertures.

An infant may be placed within the enclosure 300, with the infant's hips adjacent to support element 312 and legs positioned on upper surface 313 thereof. A user may then operate coupling members 318a, 318b, partially sealing first side 304 to the top of second side 302, accommodating the infant and support element 312 within the enclosure volume 305. First side 304 may then be located above the infant, with compartment 322 positioned proximate to the infant's torso.

The illustrated apertures 319a, 319b each extend through the first portion 306 and the second portion 308 to a bottom region or location corresponding to a region of the enclosure volume 305 configured to be at or beyond the feet of an enclosed infant. In other embodiments, one or more apertures may not be dimensioned to extend beyond a foot region of the enclosure volume 305. For example, an aperture may extend to an ankle or knee region of the enclosure volume 305. In some embodiments, the enclosure 300 may include multiple selectively openable or closable apertures wherein a length of a first aperture is less than a length of a second aperture.

With particular reference to FIG. 16, decoupling attachment members 318a, 318b allows the first side 304 to be pulled down and moved out of the way to reveal the enclosure volume 305. This configuration provides caregivers maximum visibility for proper positioning of an infant and ease of removal. In another embodiment, the first side 304 and second side 302 may be completely separated to reveal the enclosure volume 305 and may thereafter be coupled with attachment members as described herein.

Enclosure 300 further defines a neck opening 315 (FIG. 14) between the first and second sides 304, 302. The first side 304 includes a first portion 315a defining a first side of the neck opening 315 and the second side 302 includes a second portion 315b defining a second side of the neck opening 315. When the attachment members 318a, 318b are coupled to close the apertures 319a, 319b, the first portion 315a and the second portion 315b define the neck opening to allow a neck of an infant to extend from the enclosure volume 305.

Figure 17A:
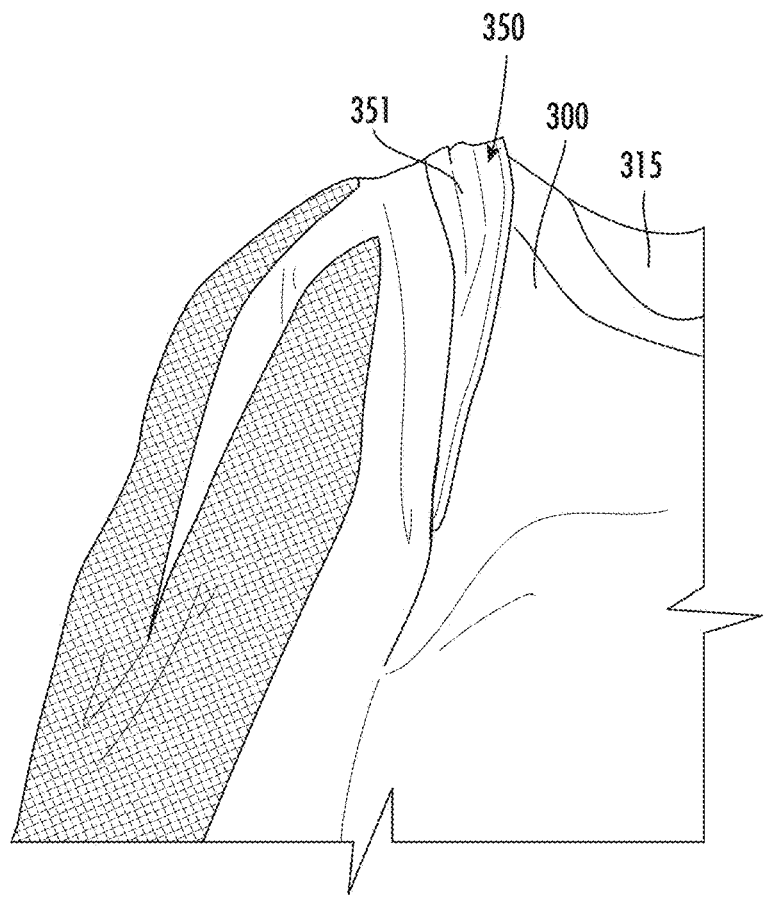
FIGS. 17A & 17B illustrate a zipper garage feature according to various embodiments described herein.
Figure 17B:
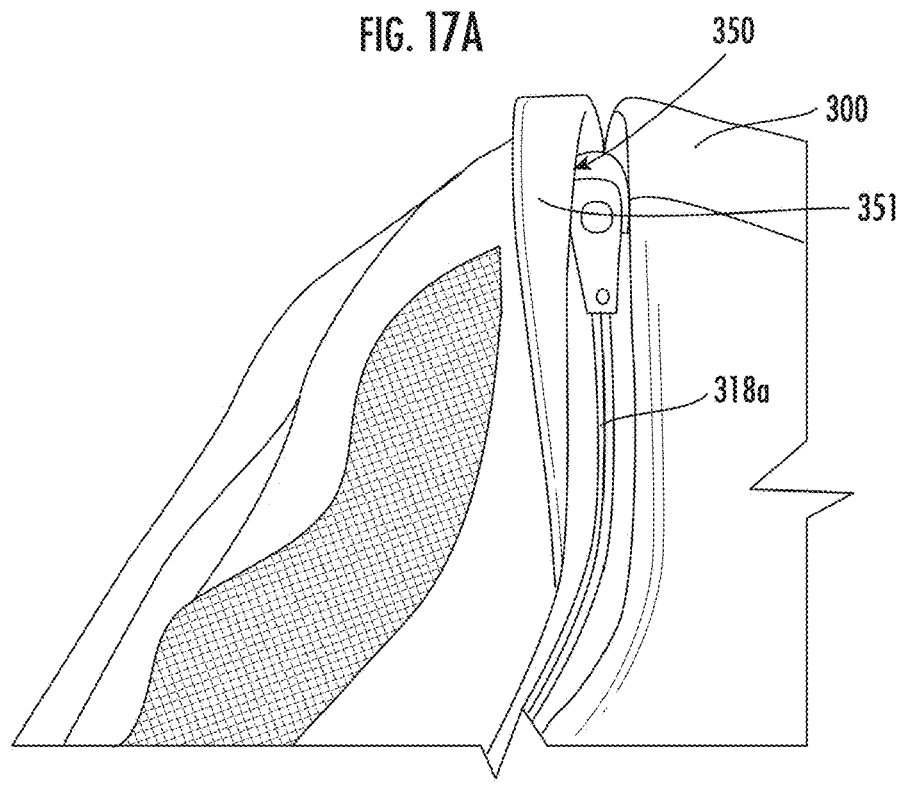

To better protect sensitive skin of an infant, all or a portion of one or more attachment members 318a, 318b may be covered interiorly. FIGS. 17A & 17B illustrate an embodiment of the enclosure 300 wherein a portion of the attachment member 318a is covered by a zipper garage 350 comprising a flap 351 configured to extend over the attachment member 318a along a portion thereof corresponding to the neck opening 315 and an adjacent region. In various embodiments, the flap 351 may include a reinforcement or biasing material configured to cover the attachment member 318a when coupled. In one embodiment, the flap 351 includes a magnet or magnetically attractive structure to attract to the attachment member 318a or a magnet or magnetically attractive structure adjacent to the attachment member 318a. In another example, the flap 351 may include an exteriorly facing attachment member such as a snap configured to mate with an adjacent interiorly facing snap to cover the attachment member 318a. While the zipper garage 350 is shown with respect to attachment member 318a, in some embodiments, a zipper garage is provided for attachment member 318b in addition to or instead of for attachment member 318a. In some embodiments, enclosure 300 does not include a zipper garage 350.

The enclosure 300 may include additional features. For example, in an embodiment, enclosure 300 may be configured to accommodate a pillow, gel pad or other type of support (not shown) beneath the head of an infant.

FIGS. 18A-22 illustrate a sleep garment 500 and methods of aiding sleep of an infant 450 utilizing a sleep garment 500. The sleep garment 500 includes an enclosure 300 as described above with respect to FIGS. 14-17B. The sleep garment 500 may also include or associate with a sleep sack 400. The sleep sack 400 may comprise a sleep sack as described in U.S. patent application Ser. No. 15/336,519, filed Oct. 27, 2016, titled Infant Calm/Sleep-Aid, SIDS Prevention Device, and Method of Use. The sleep sack 400 may comprise a body 402, which may be configured similar to body 102 and its various embodiments described herein.

In one embodiment, a method of aiding sleep of an infant 450 may include positioning an infant 450 with the enclosure volume 305 of the enclosure 300. In a further embodiment, the method may include positioning the infant 450 in a sleep sack 400 before positioning the infant in the enclosure 300.

Positioning the infant in the enclosure 300 may include laying the enclosure 300 on a surface with the exterior side of the second side 302 down. With the attachment members 318a, 318b decoupled, the first side 304 may be moved or folded down to reveal the enclosure volume 305. For example, in the illustrated enclosure 300, attachment member 318a, 318b zippers may be unzipped all the way down and the first side 304 and weight element 332 may be moved out of the way (e.g., as shown in FIG. 16). The weight element 332 may be positioned in the compartment 320 prior to or after folding down the first side 304.

Figure 18A:
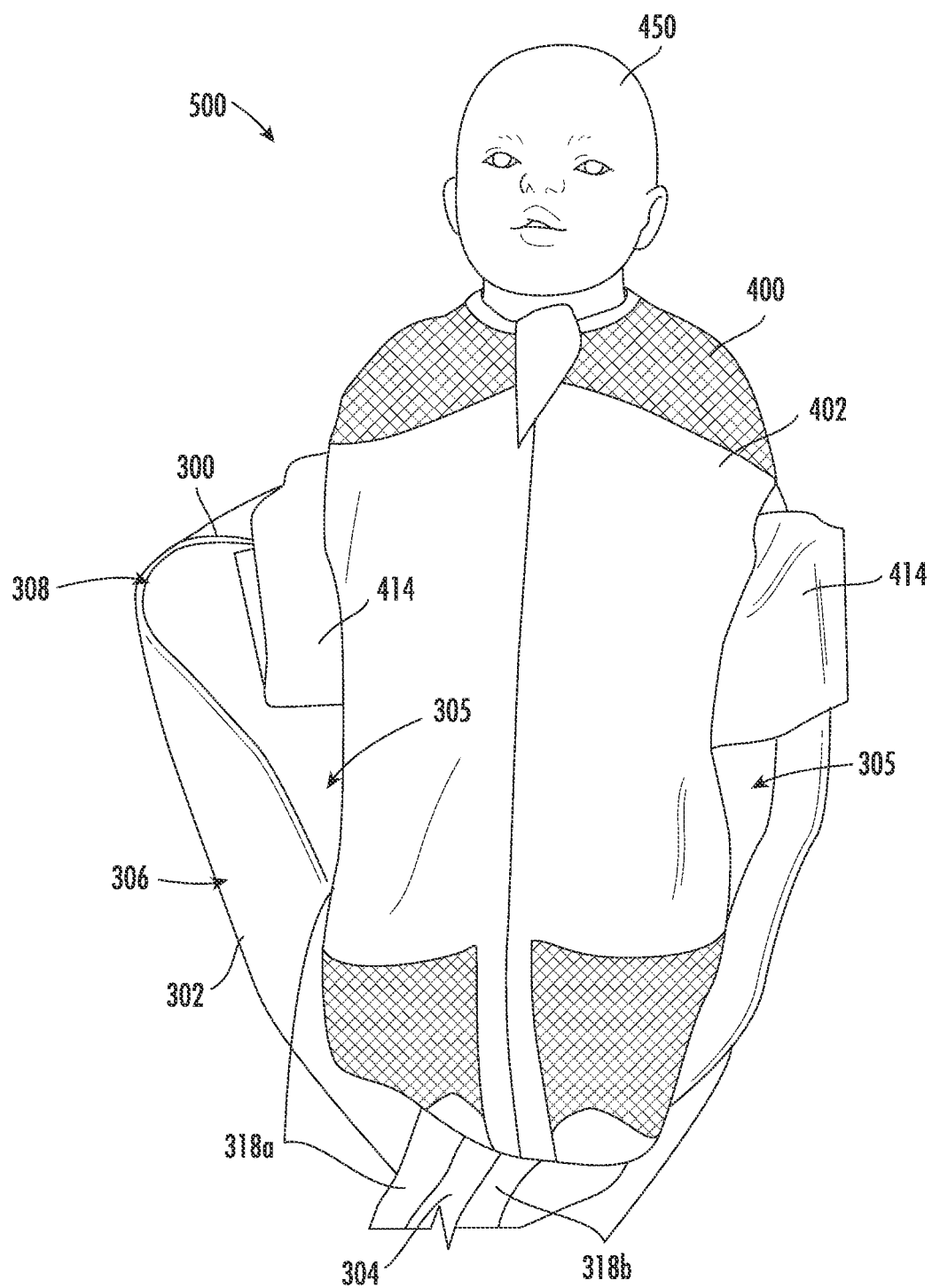
FIG. 18A is a top view of an infant positioned within an enclosure volume of an enclosure with a first side of the enclosure folded down according to various embodiments described herein.
Figure 18B:
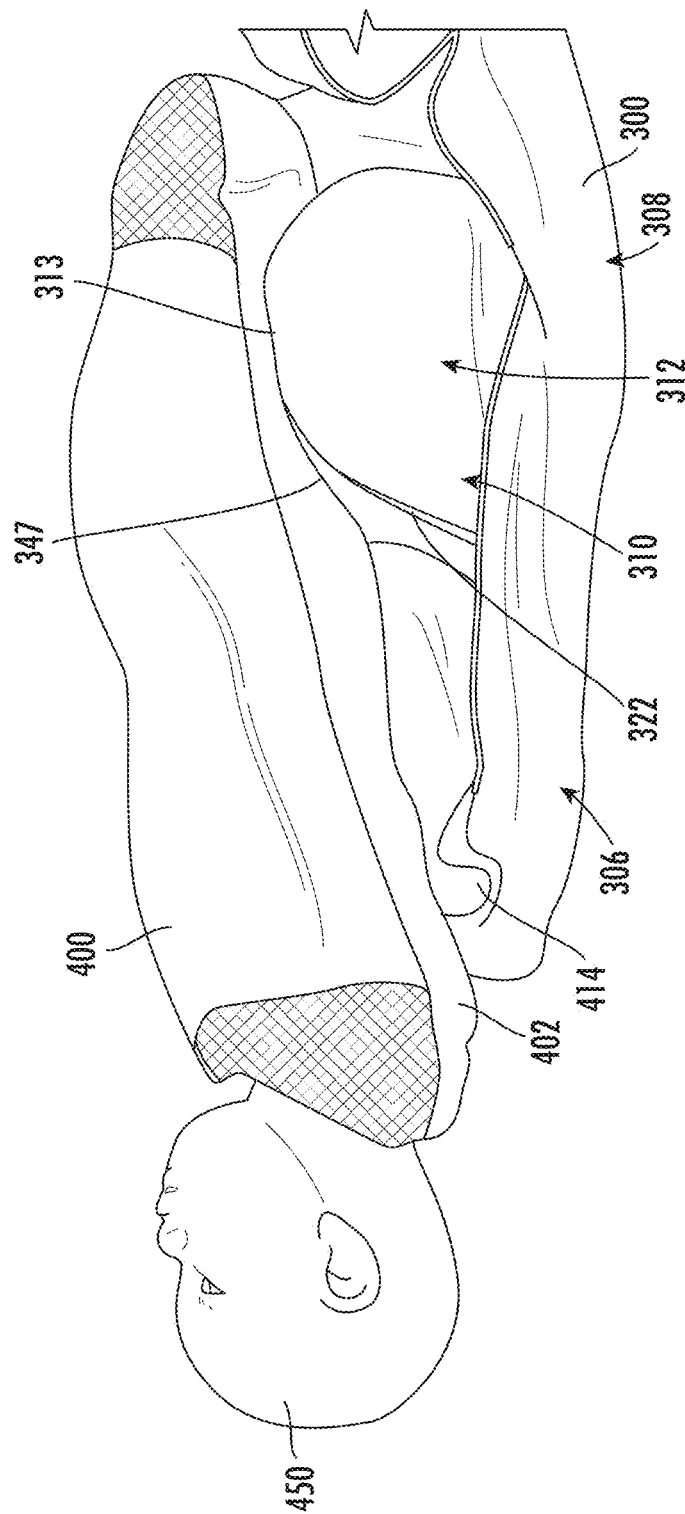
FIG. 18B is a side view of the infant positioned with the enclosure volume of the enclosure shown in FIG. 18A according to various embodiments described herein.

With the enclosure 300 open, the infant 450 may be positioned on the interior side of the second side 302 within the enclosure volume 305. FIG. 18A depicts a top view of the infant 450 positioned within the sleep sack 400 and further positioned on the interior side of the second side 302 within the enclosure volume. FIG. 18B depicts a side view of the same.

The support element 312 is preferably positioned in compartment 322 prior to positioning the infant within the enclosure. The infant 450 may be placed onto the interior side of the second side 302 with the lower body of the infant 450 up against the support element 312 and the lower legs, ankles, or feet of the infant extending over the top surface 313. In some examples, thighs may be over the top surface or the infant 450 may be placed with feet up against the support element 312. From the side view shown in FIG. 18B, the hips and feet of the infant 450 are elevated up onto the support element 312 and top surface 313 thereof. The buttocks or thighs of the infant 450 may contact a proximal surface 347 of the support element 312.

Figure 19:
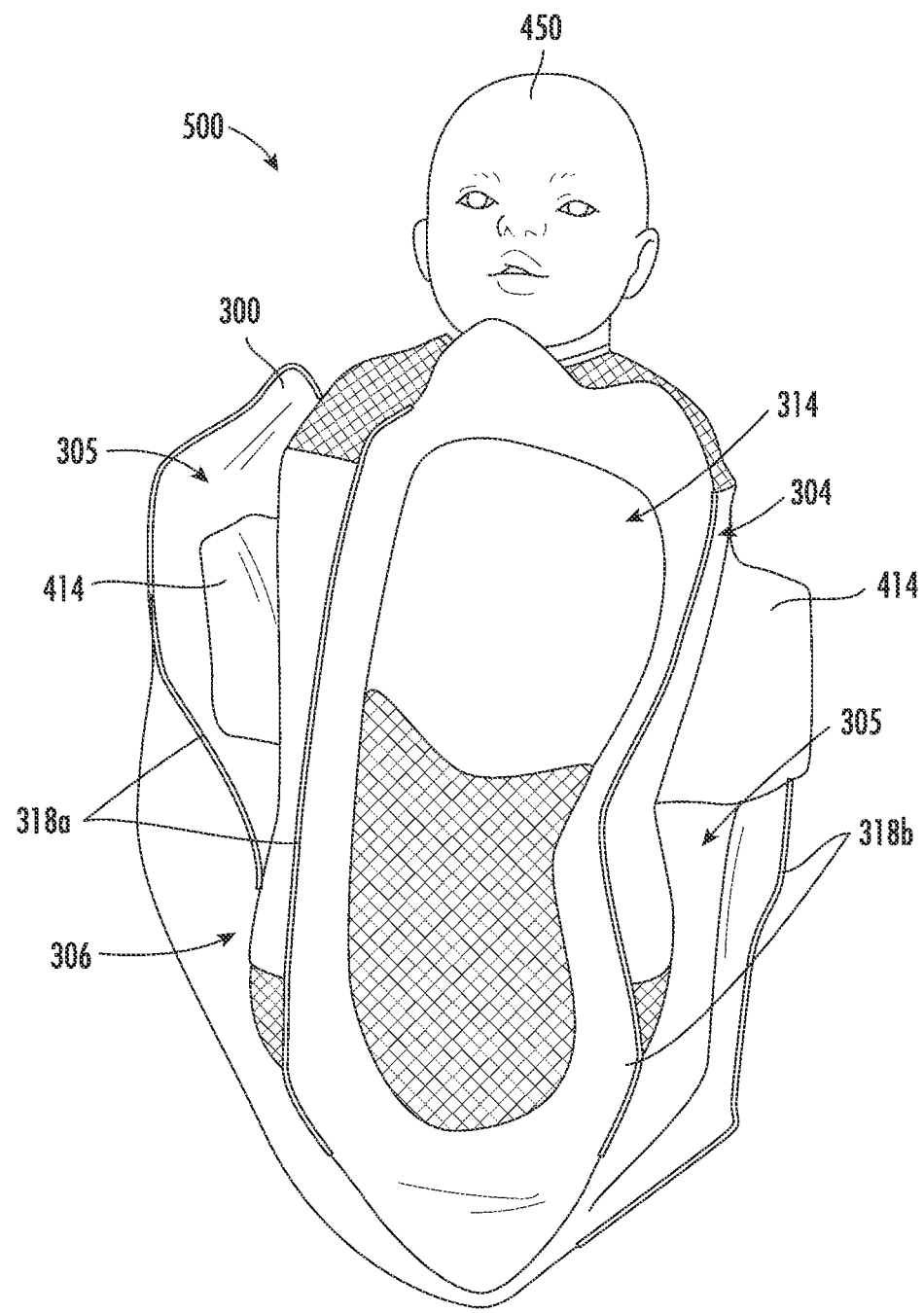
FIG. 19 is a top view of an infant positioned within an enclosure volume of an enclosure wherein a first side of the enclosure is positioned over the infant according to various embodiments described herein.
Figure 20:
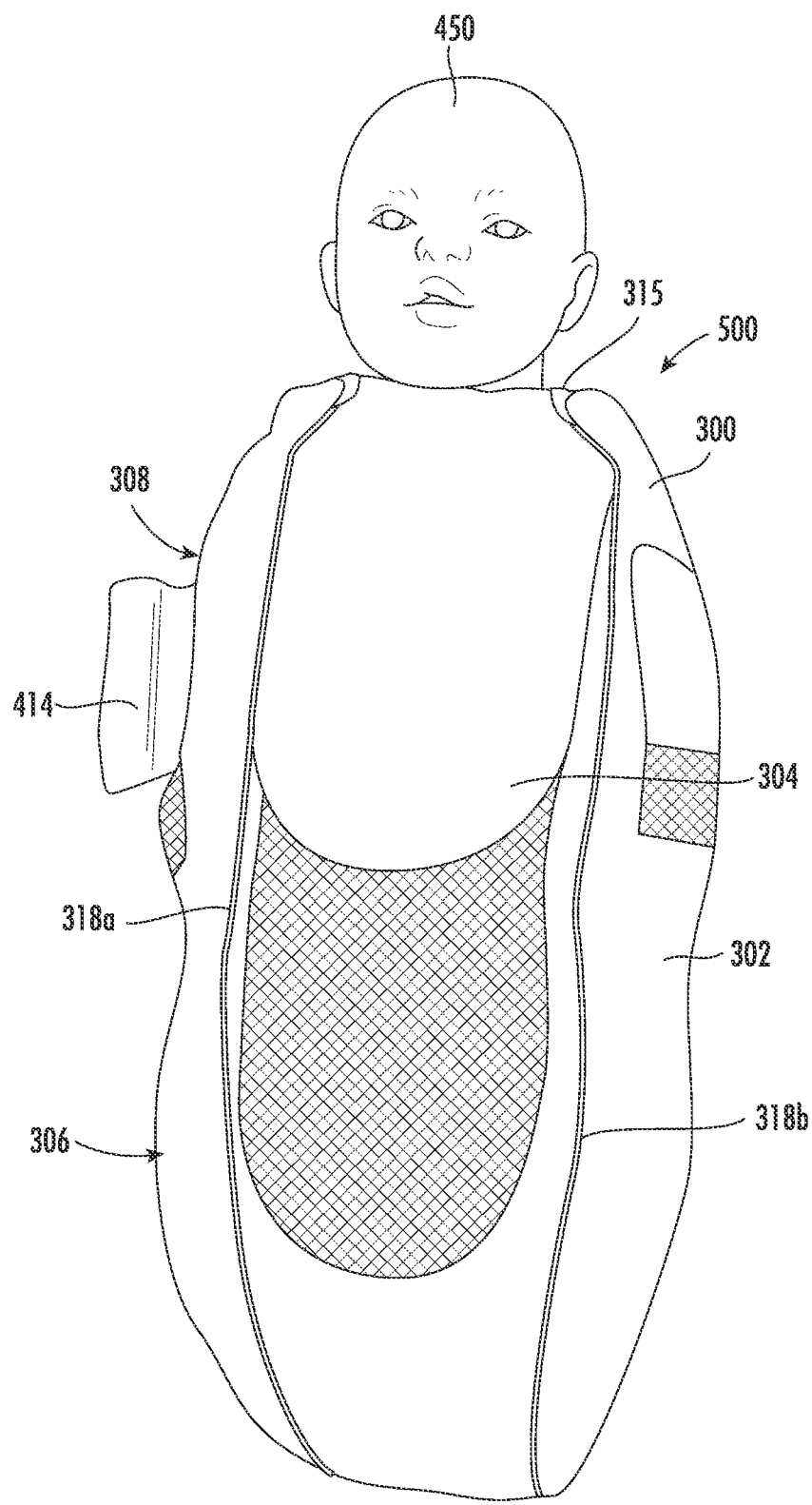
FIG. 20 is a top view of an infant secured within an enclosure volume of an enclosure according to various embodiments described herein.

With reference to FIG. 19, the first side 304 may be pulled over the infant 450 with the weight element 332 positioned over the chest/abdomen region of the infant 450. The attachment members 318a, 318b may then be coupled, e.g., zipped up, to enclose the infant 450 within the enclosure volume 305 of the enclosure 300 in a manner similar to that shown in FIG. 20.

Figure 21A:
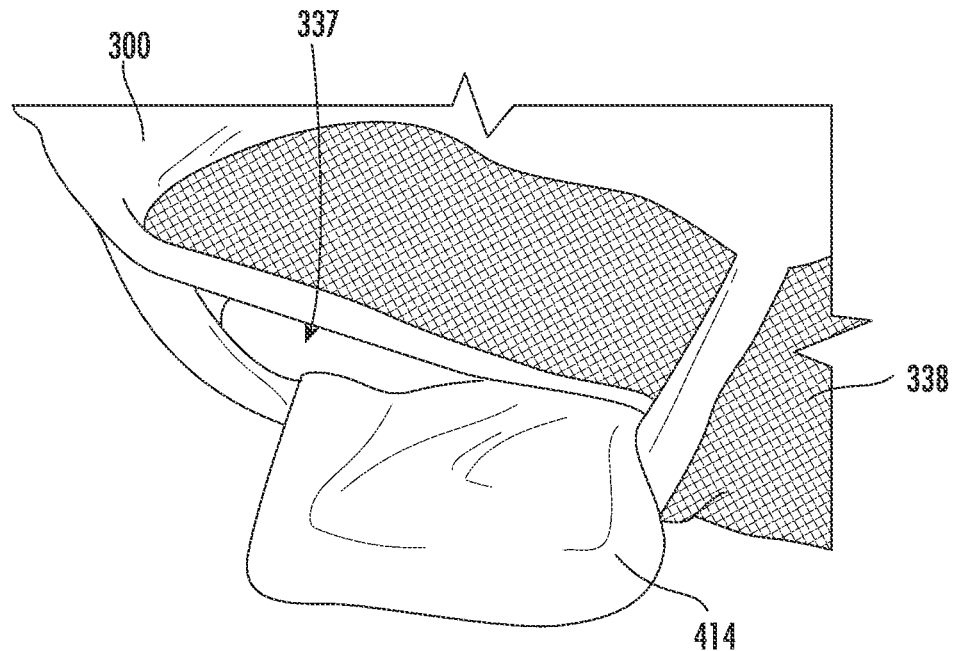
FIG. 21A illustrates a securing mechanism pulled through an opening in a side of an enclosure according to various embodiments described herein.
Figure 21B:
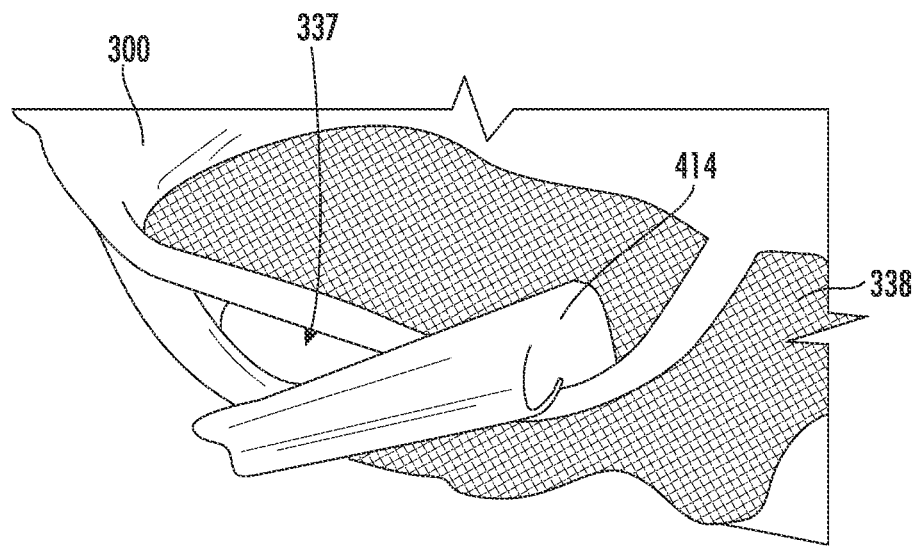
FIG. 21B illustrates a securing mechanism being pulled from a pocket in a side of the enclosure of FIG. 21A according to various embodiments described herein.

In embodiments wherein the sleep sack 400 includes one or more securing mechanisms 414, the first and second expanses of material 414a, 414b of the securing mechanism 414 may be extended out from the enclosure volume 305 through laterally positioned side openings 337 formed in the enclosure 300, as shown in FIG. 21A, for example. With reference to FIG. 21B, the enclosure 300 may also include a pocket 338 adjacent to opening 337 for tucking in the securing mechanism 414 when not in use.

It should be noted, that in some embodiments the enclosure 300 does not include side openings 337 or includes side openings 337 with attachment members to selectively open and close the openings 337. In one embodiment, the enclosure 300 includes securing mechanisms similar to that described herein with respect to sleep sacks or bodies thereof for securing the enclosure 300 to a platform or bassinet. The securing mechanism may be in addition to or instead of securing mechanism 414. In one such embodiment, the enclosure 300 includes a pocket (not shown) for tucking the securing mechanism out of the way when not in use.

Figure 22:
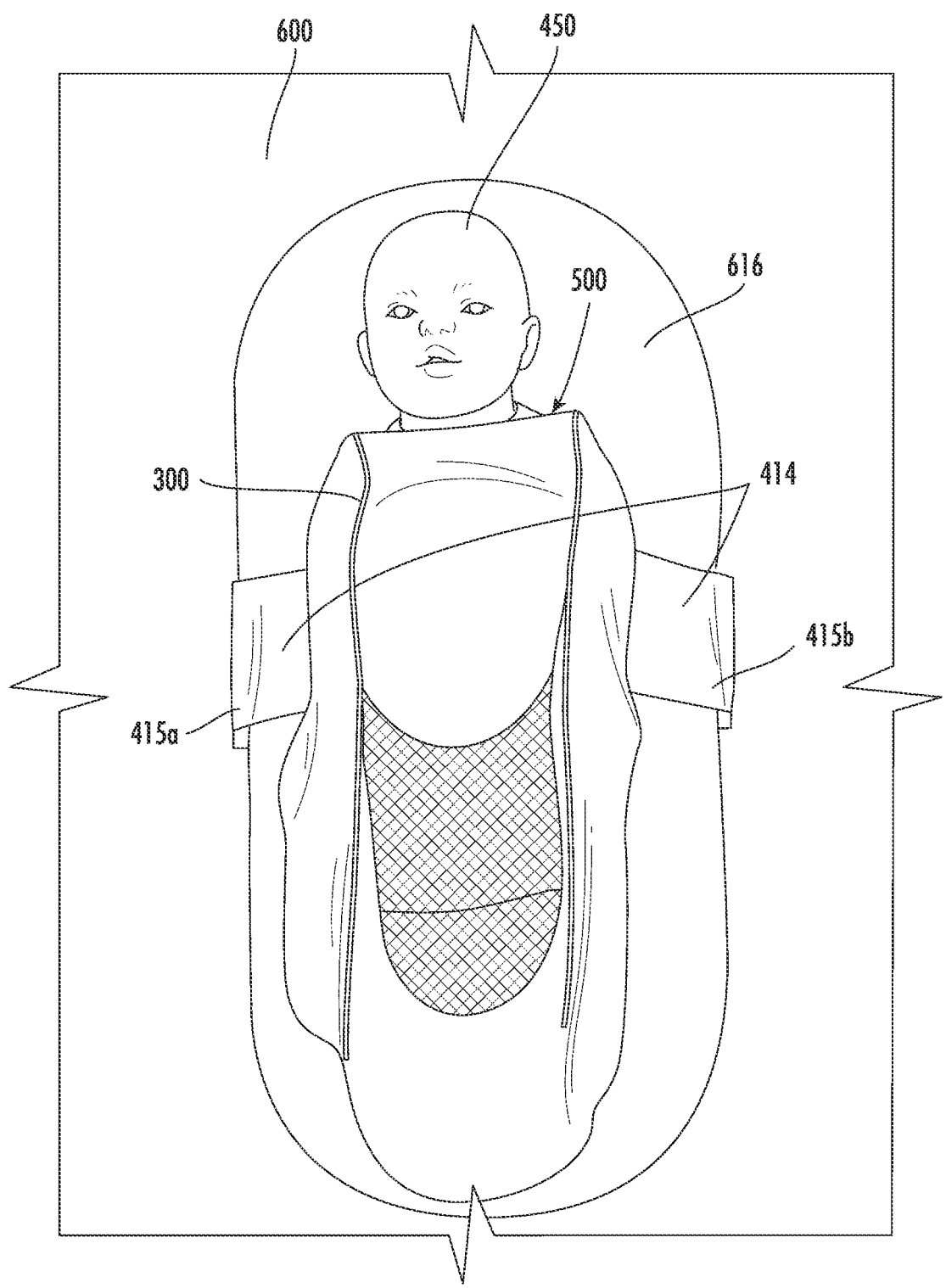
FIG. 22 is a top view of an infant positioned within an enclosure volume of an enclosure wherein the enclosure and infant are indirectly secured to a platform of a sleep device according to various embodiments described herein.

To secure the sleep garment 500 to a platform or other structure, such as a bassinet, mattress, chair, or pad, the first and second expanses of material 414a, 414b of the securing mechanism 414 may be pulled through the opening 337 or from the pocket 338 (FIGS. 21A & 21B) for coupling to or with respect to the platform or other structure. With reference to FIG. 22, the enclosure may couple to a sleep platform 616 of a sleep device 600, which is a bassinet in the illustrated embodiment. For example, securing mechanism 414 may include clips or sleeves as described above with respect to securing mechanism 114. As shown, the first and second expanses of material 414a, 414b of the securing mechanism 414 include sleeves 415a, 415b (sleeve 415a is best shown in FIG. 21B) for receiving clip arms 623a, 623b that are fixed relative to the sleep platform 616. In some embodiments, the attachment mechanism 414 or corresponding attachment mechanism to which attachment mechanism 414 couples may be configured to communicate with a control system to detect whether an attachment mechanism 414 is properly secured, and may alert a user or cease some operational function upon detecting that an attachment mechanism is not properly secured. By attaching the enclosure 300 to a sleep surface platform 616, the infant 450 accommodated within enclosure 300 may be prevented from rolling over or otherwise moving into an unsafe disposition. In various embodiments, attachment mechanism 414 and corresponding attachment mechanisms to which attachment mechanism 414 couples may correspond to attachment mechanisms described in U.S. patent application Ser. No. 15/336,519, filed Oct. 27, 2016, titled Infant Calm/Sleep-Aid, SIDS Prevention Device, and Method of Use. In one embodiment, the sleep device comprises a sleep device or bassinet having a movable platform as described in U.S. patent application Ser. No. 15/336,519, filed Oct. 27, 2016, titled Infant Calm/Sleep-Aid, SIDS Prevention Device, and Method of Use.

It is to be appreciated that embodiments of the sleep garment 500 may include fewer or additional features. For example, in one embodiment, the sleep garment 500 does not include a sleep sack 400. In some such embodiments, the sleep garment 500 may include another sack or swaddling device or may not include an enclosure to enclose the infant in addition to that of the enclosure 300. In some embodiments, the infant may be enclosed in the enclosure 300 without being enclosed in a sleep sack or swaddle. As described above, the sleep garment 500 or enclosure 300 may also be configured with fewer or additional accommodation mechanisms.

Embodiments of the sleep garment 500 may include modifications to the sleep sack 400, enclosure 300, or both. The modifications may include any of those described herein, including those described with respect to sleep garment 100, body 102, enclosure 200, or outer enclosure 120. For example, the support element 312 may be incorporated under the lower body, legs, or feet of the infant within the interior of the sleep sack 400 or a compartment thereof. The support element 312 may be positioned loosely or unattached with respect to the enclosure 300. The weight element 332 may be attached to or within a compartment of the sleep sack 400. The weight element 332 may be positioned at other locations to apply weight to other regions of the body of the infant.

In an embodiment, the enclosure 300 may be configured to receive a weight element 332 at a location to thereby apply pressure to the infant's upper body, lower body, or both upper and lower body simultaneously. In one embodiment, a sleep sack 400 or body 402 may include an accommodation mechanism, which may be in addition to or instead of one or both of accommodation mechanisms 314, 310. For example, a body 302 may include a weight element, support element, or both, which may be similar to weight element 332 and support element 312. Such elements may be coupled or couplable to the body 302, e.g., elements may be attachable to surfaces via attachment members such as snaps, hook and loop, straps, or the like or may be received within compartments such as a pocket. In some embodiments, one or more accommodation mechanisms may be loosely positioned within the enclosure volume 305 or exterior thereto and located to elevate the lower body, legs, or feet or apply weight to the chest of an infant in a manner consistent to that described herein.

As noted above, body 102 described with respect to FIGS. 1-5, may be used to enclose an infant and subsequently be enclosed within the enclosure volume 305 of enclosure 300 (not shown). In one such embodiment, the weight element 332, rather than being received at location 335, may be received on body 102 at location 134 proximate to the second portion 112 at the first side 104 of the body 102 by connecting the weight element 332 to the second portion 112 by a connector which may include but is not limited to any of the following: a strap configured to attach to a clip, an elastic strap, a hook and loop attachment mechanism, a push snap attachment, a zipper mechanism, a magnetic attachment mechanism, or any similar mechanism.

In an embodiment, sleep garment 500 may be configured to accommodate a pillow, gel pad or other type of support (not shown) beneath the head of an infant.

Figure 23A:
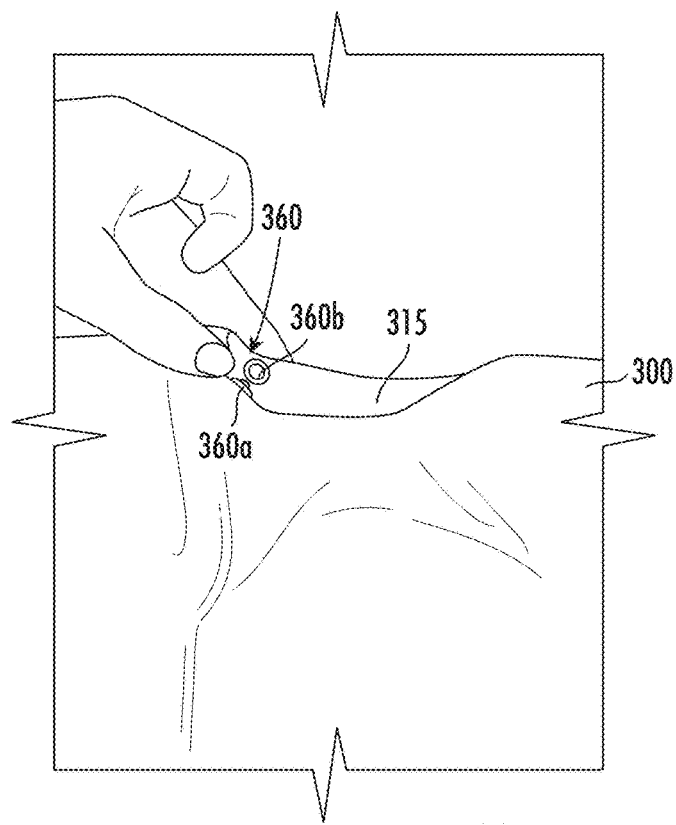
FIGS. 23A & 23B illustrate a neck opening adjustment mechanism according to various embodiments described herein.
Figure 23B:
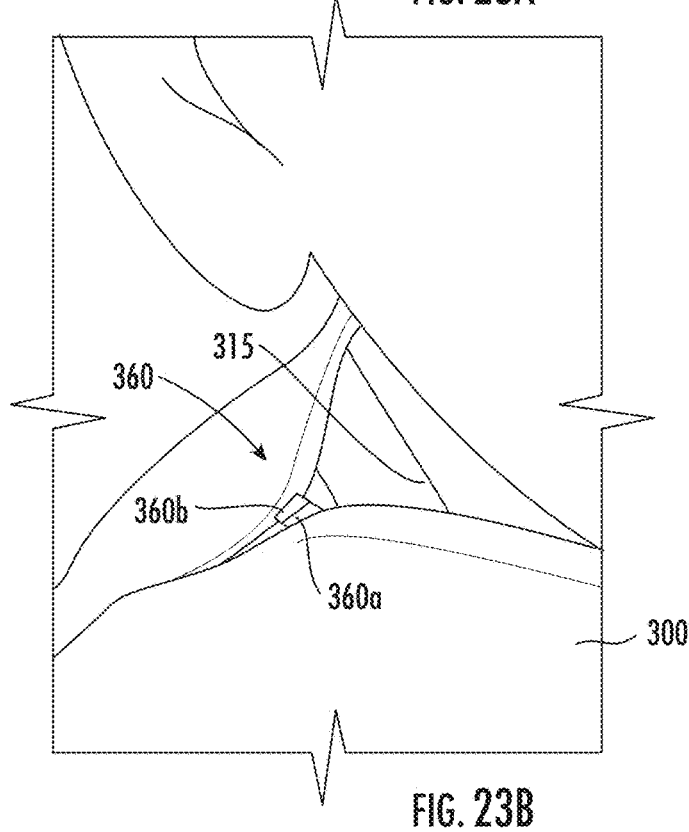

In some embodiments, the enclosure 300 includes a neck opening adjustment mechanism operable to adjust the size of the neck opening 315. FIGS. 23A & 23B illustrate a neck opening adjustment mechanism 360 according to various embodiments. As shown in FIG. 23A, adjacent sides of the neck opening 315 include attachment members 360a, 360b, which in this embodiment comprise snaps. The attachment members 360a, 360b may be coupled to decrease the size of the neck opening 315, as exemplified in FIG. 23B. For infants with larger necks, attachment members 360a, 360b may be left decoupled to provide a larger neck opening 315. While the neck opening adjustment mechanism 360 is shown with respect to attachment members 360a, 360b comprising snaps, in some embodiments, attachment members 360a, 360b may comprise straps, clips, hook and loop, mating structures, or other coupling structures. Additionally, while the neck opening adjustment mechanism 360 is shown with respect to a single side of the neck opening 315, in various embodiments, the neck opening adjustment mechanism 360 may include adjustment features on a second side of the opening comprising attachment members.

In various embodiments, a method of aiding sleep with respect to an infant that prefers a side or stomach position, which is unsafe and known to increase incidence of SIDS, includes enclosing the infant within a sleep garment or enclosure as described herein to cause the infant feel as if they are in the fetal position, but while sleeping safely on the back. The method may similarly be effective to aid sleep of infants that have difficulty sleeping on their back or when not laying on a caregiver's body. The method may also be effective to aid sleep of infants that experience limited sleep duration or those that sleep well in a rock in play, swing or bouncer, but not on their back.

This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this specification. Thus, it is contemplated and understood that this specification supports additional embodiments not expressly set forth in this specification. Such embodiments may be obtained, for example, by combining, modifying, or re-organizing any of the disclosed steps, components, elements, features, aspects, characteristics, limitations, and the like, of the various non-limiting and non-exhaustive embodiments described in this specification.

Various elements described herein have been described as alternatives or alternative combinations, e.g., in a lists of selectable actives, ingredients, or compositions. It is to be appreciated that embodiments may include one, more, or all of any such elements. Thus, this description includes embodiments of all such elements independently and embodiments including such elements in all combinations.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an application of the described embodiments. Further, the use of a singular noun includes the plural, and the use of a plural noun includes the singular, unless the context of the usage requires otherwise. Additionally, the grammatical conjunctions "and" and "or" are used herein according to accepted usage. By way of example, "x and y" refers to "x" and "y". On the other hand, "x or y" refers to "x", "y", or both "x" and "y", whereas "either x or y" refers to exclusivity.

Any numerical range recited herein includes all values and ranges from the lower value to the upper value. For example, if a range is stated as 1 to 50, it is intended that values such as 2 to 40, 10 to 30, 1 to 3, or 2, 25, 39 and the like, are expressly enumerated in this specification. These are only examples of what is specifically intended, and all possible combinations of numerical values and ranges between and including the lowest value and the highest value enumerated are to be considered to be expressly stated in this application. Numbers modified by the term "approximately" are intended to include +/−10% of the number modified.

The present disclosure may be embodied in other forms without departing from the spirit or essential attributes thereof and, accordingly, reference should be had to the following claims rather than the foregoing specification as indicating the scope of the invention. Further, the illustrations of arrangements described herein are intended to provide a general understanding of the various embodiments, and they are not intended to serve as a complete description. Many other arrangements will be apparent to those of skill in the art upon reviewing the above description. Other arrangements may be utilized and derived therefrom, such that logical substitutions and changes may be made without departing from the scope of this disclosure.

What is claimed is:

1. An infant sleep garment comprising:
   a sleep sack comprising:
      a body having a front side and a back side, the front side and the back side together defining an interior volume configured to enclose an upper body and lower body of the infant therein, wherein the lower body includes a waist, legs, and feet of the infant; and
      a securing mechanism configured to secure the sleep sack on a sleep surface, the securing mechanism comprising a first expanse of material connected to the body and extending outwardly from a first lateral side of the body, and a second expanse of material extending from a second lateral side of the body, the securing mechanism located on the back side of the body; and
   an enclosure having a first side and a second side, the first side and the second side together defining an enclosure volume therebetween configured to receive the sleep sack, wherein the enclosure comprises:
      a first portion configured to accommodate a portion of the sleep sack within the enclosure volume that corresponds to that which encloses the lower body of the infant when the infant is enclosed within the sleep sack;
      a second portion located in a superior position relative to the first portion and configured to accommodate a portion of the sleep sack corresponding to that which encloses the upper body of the infant when the infant is enclosed within the sleep sack;
      a weight element coupled or couplable to the first side along the second portion;
      a support element coupled or couplable to the second side along the first portion at a location corresponding to the lower body of the infant when the infant is enclosed within the sleep sack and the sleep sack is received within the enclosure volume, wherein the support element is configured to elevate the legs and the feet of the infant relative to the at least a portion of the upper body of the infant; and first and second lateral sides, wherein the first lateral side includes a first opening that is positioned at a location corresponding to the first expanse of material when the sleep sack is received within the enclosure volume and the second lateral side includes a second opening that is positioned at a location corresponding to the second expanse of material when the sleep sack is received within the enclosure volume, and wherein the first opening and the second opening are configured to provide a passage through which the respective first and second expanses of material may be extended to an exterior side of the enclosure from the enclosure volume to secure the sleep sack on the sleep surface while received within the enclosure volume.

2. The infant sleep garment of claim 1, wherein the weight element weighs between 0.5 pounds and 2 pounds, and wherein the support element includes an arcuate shaped cross-section that extends a distance into the enclosure volume at least 4 inches.

3. The infant sleep garment of claim 1, wherein the enclosure further comprises first and second pockets adjacent to the respective first and second openings for tucking away the respective first and second material expanses when not in use.

4. An infant sleep garment comprising:
a sleep sack comprising:
   a body having a front side and a back side, the front side and the back side together defining an interior volume configured to enclose an upper body and lower body of the infant therein; and
   a securing mechanism configured to secure the sleep sack on a sleep surface, the securing mechanism comprising a first expanse of material connected to the body and extending outwardly from a first lateral side of the body, and a second expanse of material extending from a second lateral side of the body, the securing mechanism located on the back side of the body; and
an enclosure having a first side and a second side, the first side and the second side together defining an enclosure volume therebetween configured to receive the sleep sack, wherein the enclosure comprises:
   a first portion configured to accommodate a portion of the sleep sack within the enclosure volume that corresponds to the lower body of an infant when the infant is enclosed within the sleep sack; and
   a second portion located in a superior position relative to the first portion and configured to accommodate a portion of the sleep sack within the enclosure volume that corresponds to at least a portion of the upper body of the infant when the infant is enclosed within the sleep sack;
   wherein the first side is configured to couple with a weight element along the second portion to position the weight element to apply weight to at least a portion of the upper body of the infant when the sleep sack encloses the infant within the interior volume and is received within the enclosure volume, and wherein the second side is configured to couple with a support element along the first portion at a location configured to position the support element under the lower body of the infant to elevate hips and feet of the infant relative to the at least a portion of the upper body of the infant when the sleep sack encloses the infant within the interior volume and is received within the enclosure volume; and first and second lateral sides, wherein the first lateral side includes a first opening that is positioned at a location corresponding to the first expanse of material when the sleep sack is received within the enclosure volume and the second lateral side includes a second opening that is positioned at a location corresponding to the second expanse of material when the sleep sack is received within the enclosure volume, and wherein the first opening and the second opening are configured to provide a passage through which the respective first and second expanses of material may be extended to an exterior side of the enclosure from the enclosure volume to secure the sleep sack on the sleep surface while received within the enclosure volume.

5. The infant sleep garment of claim 4, wherein the first side includes a compartment configured to receive the weight element to thereby couple the weight element at the first side.

6. The infant sleep garment of claim 4, wherein the first side is configured to couple with the weight element at a location corresponding to a chest or abdominal area of the infant to apply pressure to the same when the sleep sack is received within the enclosure volume and the infant is enclosed within the interior volume of sleep sack.

7. The infant sleep garment of claim 6, wherein the first side includes a compartment configured to receive the weight element to thereby couple the weight element at the first side.

8. The infant sleep garment of claim 4, wherein the second side includes a compartment configured to receive the support element.

9. The infant sleep garment of claim 8, wherein the compartment configured to receive the support element is positioned at a location along the second side corresponding to at least thighs and feet of the infant to underlay the same when the sleep sack is received within the enclosure volume and the infant is enclosed within the interior volume of sleep sack.

10. The infant sleep garment of claim 8, wherein the compartment configured to receive the support element is positioned at a location along the second side corresponding to at least hips of the infant to underlay the same when the sleep sack is received within the enclosure volume and the infant is enclosed within the interior volume of sleep sack.

11. The infant sleep garment of claim 4, wherein, when coupled at the second side, the support element extends 4.5 to 5.5 inches into the enclosure volume.

12. The infant sleep garment of claim 11, wherein the support element includes a cylindrical portion that, when coupled at the second side, extends into the enclosure volume.

13. The infant sleep garment of claim 12, wherein, when coupled at the second side, an arcuate shaped cross-section portion of the support element extends 4.5 to 5.5 inches into the enclosure volume.

14. The infant sleep garment of claim 4, wherein the first side and the second side are selectively couplable along their respective lateral peripheries extending between the first and second portions, and wherein adjacent lateral peripheries of the first and second sides include attachment members configured to couple the adjacent lateral peripheries.

15. The infant sleep garment of claim 14, wherein the attachment members comprise zipper halves that are matable with adjacent zipper to couple the lateral peripheries.

16. The infant sleep garment of claim 4, wherein the first side includes a compartment configured to receive the weight element to thereby couple the weight element at the first side, and the second side includes a compartment configured to receive the support element,
 wherein the compartment configured to receive the weight element is positioned along the first side at a location corresponding to a chest or abdominal area of the infant when the sleep sack is received within the enclosure volume and the infant is enclosed within the interior volume of sleep sack such that the weight element applies pressure to the same when received therein,
 wherein the compartment configured to receive the support element is positioned along the second side at a location to underlay the lower body of the infant when the sleep sack is received within the enclosure volume and the infant is enclosed within the interior volume of sleep sack, and
 wherein, when received within the compartment, the support element extends a distance into the enclosure volume between 4.5 to 5.5 inches.

17. The infant sleep garment of claim 4, wherein the enclosure further comprises first and second pockets adjacent to the respective first and second openings for tucking away the respective first and second material expanses when not in use.

18. An infant sleep garment comprising:
 a sleep sack comprising:
  a body having a front side and a back side, the front side and the back side together defining an interior volume configured to enclose an upper body and lower body of the infant therein; and
  a securing mechanism configured to secure the sleep sack on a sleep surface, the securing mechanism comprising a first expanse of material connected to the body and extending outwardly from a first lateral side of the body, and a second expanse of material extending from a second lateral side of the body, the securing mechanism located on the back side of the body; and
 an enclosure having a first side and a second side, the first side and the second side together defining an enclosure volume therebetween configured to receive the sleep sack, wherein the enclosure comprises:
  a first portion configured to accommodate a portion of the sleep sack within the enclosure volume that corresponds to the lower body of an infant when the infant is enclosed within the sleep sack; and
  a second portion located in a superior position relative to the first portion and configured to accommodate a portion of the sleep sack within the enclosure volume that corresponds to the upper body of the infant when the infant is enclosed within the sleep sack and to therein enclose arms and hands of the infant within the enclosure volume;
  first and second lateral sides, wherein the first lateral side includes a first opening that is positioned at a location corresponding to the first expanse of material when the sleep sack is received within the enclosure volume and the second lateral side includes a second opening that is positioned at a location corresponding to the second expanse of material when the sleep sack is received within the enclosure volume, and wherein the first opening and the second opening are configured to provide a passage through which the respective first and second expanses of material may be extended to an exterior side of the enclosure from the enclosure volume to secure the sleep sack on the sleep surface while received within the enclosure volume; and
  at least one element selected from of:
   a weight element is coupled or couplable to the first side along the second portion at a location corresponding to an abdominal or chest area of the infant when the infant is enclosed within the sleep sack and the sleep sack is received within the enclosure volume, wherein the weight element weighs between 1 pound and 1.5 pounds; and
   a support element configured to elevate hips and feet of the infant relative to the at least a portion of the upper body of the infant and is coupled or couplable to the second side along the first portion at a location corresponding to at least a portion of the lower body of the infant when the infant is enclosed within the sleep sack and the sleep sack is received within the enclosure volume.

19. The infant sleep garment of claim 18, wherein the infant sleep garment comprises the support element, wherein the support element includes an arcuate shaped cross-section that extends a distance into the enclosure volume at least 4 inches.

20. The infant sleep garment of claim 18, wherein the enclosure further comprises first and second pockets adjacent to the respective first and second openings for tucking away the respective first and second material expanses when not in use.

* * * * *